United States Patent
Conner et al.

(10) Patent No.: US 12,048,442 B2
(45) Date of Patent: Jul. 30, 2024

(54) FEMORAL FINISHING RASP

(71) Applicant: DEPUY SYNTHES PRODUCTS, INC., Raynham, MA (US)

(72) Inventors: Nathanael K. Conner, Fort Wayne, IN (US); Cory A. Shulaw, Warsaw, IN (US); Jon M. Edwards, Stuart, FL (US); Matthew S. Wallace, Wellington, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 197 days.

(21) Appl. No.: 17/569,991

(22) Filed: Jan. 6, 2022

(65) Prior Publication Data

US 2023/0210543 A1 Jul. 6, 2023

(51) Int. Cl.
*A61B 17/16* (2006.01)
*A61B 17/92* (2006.01)
*A61F 2/36* (2006.01)

(52) U.S. Cl.
CPC .......... *A61B 17/1659* (2013.01); *A61B 17/92* (2013.01); *A61F 2/3662* (2013.01)

(58) Field of Classification Search
CPC .......... A61B 17/1659; A61B 17/1675
See application file for complete search history.

(56) References Cited

U.S. PATENT DOCUMENTS

| 5,417,693 | A | * | 5/1995 | Sowden | A61F 2/461 269/238 |
| 5,553,476 | A | * | 9/1996 | Oehy | B21D 31/00 72/325 |
| 2004/0243134 | A1 | * | 12/2004 | Walker | A61B 17/1659 606/79 |
| 2005/0192584 | A1 | * | 9/2005 | Walker | A61B 17/1675 606/79 |

FOREIGN PATENT DOCUMENTS

EP  1550418 A1  7/2005

OTHER PUBLICATIONS

International Search Report for Application No. PCT/IB2022/062459 dated Mar. 6, 2023, 6 pages.

* cited by examiner

*Primary Examiner* — David W Bates
(74) *Attorney, Agent, or Firm* — Barnes & Thornburg LLP

(57) ABSTRACT

A femoral finishing rasp assembly for use in an orthopaedic surgical procedure includes a femoral finishing rasp and an impactor adaptor. The femoral finishing rasp includes femoral-facing anterior and posterior surfaces, each of which includes a corresponding set of rasping teeth. The impactor adaptor is configured to couple to an exterior surface of the femoral finishing rasp and to an orthopaedic impactor to facilitate the use of the femoral finishing rasp on a distal end of a patient's surgically-prepared femur. A method for performing an orthopaedic surgical procedure using the femoral finishing rasp assembly is also disclosed.

19 Claims, 19 Drawing Sheets

FEMORAL FINISHING RASP

TECHNICAL FIELD

The present disclosure relates generally to orthopaedic surgical instruments for performing an orthopaedics surgical procedure and, more particularly, to femoral rasps for use on a patient's femur.

BACKGROUND

Joint arthroplasty is a well-known surgical procedure by which a diseased and/or damaged natural joint is replaced by a prosthetic joint. A typical knee prosthesis, for example, includes a tibial tray, a femoral component, and a polymer insert or bearing positioned between the tibial tray and the femoral component. Depending on the severity of the damage to the patient's joint, orthopaedic prostheses of varying mobility may be used. For example, the knee prosthesis may include a "fixed" tibial insert in cases wherein it is desirable to limit the movement of the knee prosthesis, such as when significant soft tissue damage or loss is present. Alternatively, the knee prosthesis may include a "mobile" tibial insert in cases wherein a greater degree of freedom of movement is desired. Additionally, the knee prosthesis may be a total knee prosthesis designed to replace the femoral-tibial interface of both condyles of the patient's femur or a uni-compartmental (or uni-condylar) knee prosthesis designed to replace the femoral-tibial interface of a single condyle of the patient's femur.

The type of orthopedic knee prosthesis used to replace a patient's natural knee may also depend on whether the patient's posterior cruciate ligament is retained or sacrificed (i.e., removed) during surgery. For example, if the patient's posterior cruciate ligament is damaged, diseased, and/or otherwise removed during surgery, a posterior-stabilized knee prosthesis may be used to provide additional support and/or control at later degrees of flexion. Alternatively, if the posterior cruciate ligament is intact, a cruciate-retaining knee prosthesis may be used.

To facilitate the replacement of a patient's natural joint (e.g., the patient's knee joint) with a corresponding orthopaedic prosthesis, orthopaedic surgeons may use a variety of orthopaedic surgical instruments such as, for example, saws, reamers, drills, broaches, impactors, and/or other surgical instruments. In certain situations, some bone cuts or resections may be inaccurate or otherwise vary from the orthopaedic surgical plan due to various factors including saw blade deflection, cutting block movement, and/or relative tilting of the saw blade to the corresponding cutting slot. In such cases, the orthopaedic surgeon may use a bone rasp or file to manually clean up and/or sculpt the corresponding bone.

SUMMARY

According to an aspect of the present disclosure, a femoral finishing rasp assembly for use in an orthopaedic surgical procedure may include a femoral finishing rasp and an impactor adaptor. The femoral finishing rasp may has a body that defines an interior cavity configured to receive a distal end of a patient's femur. The body may include an anterior wall having an interior surface facing the interior cavity and an exterior surface opposite the interior surface, a posterior wall opposite the anterior wall and having an interior surface facing the interior cavity and an exterior surface opposite the interior surface of the posterior wall, a distal wall having an anterior end connected to a distal end of the anterior wall and a posterior end connected to a distal end of the posterior wall, and a connector attached to the exterior surface of the distal wall. The interior surface of the anterior wall may include a first set of rasping teeth, and the interior surface of the posterior wall may include a second set of rasping teeth. Additionally, the distal wall may include an interior surface facing the interior cavity and an exterior surface opposite the interior surface of the distal wall. The impactor adaptor may include a first end configured to be coupled to an orthopaedic impactor and a second end, opposite the first end, having a connector configured to selectively couple to the connector of the femoral finishing rasp.

In some embodiments, the first set of rasping teeth and the second set of rasping teeth are arranged or oriented to face in the proximal direction away from the body of the femoral finishing rasp. In such embodiments, the first and second set of rasping teeth may be configured to rasp a bone of a patient in a proximal-distal direction. In other embodiments, the first set of rasping teeth and the second set of rasping teeth are arranged or oriented to face in the distal direction toward the body of body of the femoral finishing rasp.

In some embodiments, the connector of the femoral finishing rasp may include a medial bracket extending distally from the exterior surface of the distal wall and a lateral bracket extending distally from the exterior surface of the distal wall. In such embodiments, the medial and lateral brackets may be laterally spaced from each other, and each medial and lateral bracket may include a corresponding aperture defined therethrough, The aperture of the medial bracket and the aperture of the lateral bracket may be coaxial with each other. In such embodiments, the distal wall may also include an aperture defined therethrough and located between the medial bracket and the lateral bracket.

Additionally, in some embodiments, the posterior wall may include an aperture defined therethrough and in fluid communication with the aperture of the distal wall. In such embodiments, the posterior wall may include a medial posterior wall and a lateral posterior wall laterally spaced from the medial posterior wall by the aperture of the posterior wall. The distal wall may also include a plurality of interior surfaces that cooperate to define the aperture of the distal wall and, in such embodiments, at least one of the interior surfaces defines a femoral cutting guide. For example, the plurality of interior surfaces of the distal wall may cooperate to define a femoral box cutting guide.

In some embodiments, the connector of the femoral finishing rasp further may include a plurality of sidewalls that cooperate with the medial bracket and the lateral bracket to define a recess configured to receive a head of the connector of the impactor adaptor. Additionally, in some embodiments, the connector of the impactor adaptor may include a first and second tab, and each of the first and second tabs may include a catch. In such embodiments, when the connector of the impactor adaptor is coupled to the connector of the femoral finishing rasp, the catch of the first tab may be received in the aperture of the medial bracket of the connector of the femoral finishing rasp, and the catch of the second tab may be received in the aperture of the lateral bracket of the connector of the femoral finishing rasp. Additionally, in such embodiments, the first tab and the second tab may be biased outwardly away each other, and each of the first tab and the second tab may be movable in an inwardly direction to cause movement of the associated catch from the aperture of the corresponding medial and lateral bracket to decouple the connector of the impactor adaptor from the connector of the femoral finishing rasp.

In some embodiments, the connector of the impactor adaptor may include a pair of tracks, and each of the first tab and the second tab may be positioned in a corresponding track of the pair of tracks. In such embodiments, the first tab and the second tab may be movable in the corresponding track to couple or decouple the connector of the impactor adaptor and the connector of the femoral finishing rasp.

Additionally, in some embodiments, the femoral finishing rasp may further include a securing device. In such embodiments, the distal wall of the femoral finishing rasp may include a passageway defined therethough, and the second end of the impactor adaptor may include an aperture defined therein. The securing device may be configured to be received through the passageway of the distal wall and into the aperture of the second end of the impactor adaptor to secure the femoral finishing ramp to the impactor adaptor.

According to another aspect of the present disclosure, a femoral finishing rasp assembly for use in an orthopaedic surgical procedure may include a femoral finishing rasp and an impactor adaptor. The body of the femoral finishing rasp may include an articular side and a rasping side opposite the articular side. The articular side may include a medial femoral condyle surface having a curved contour and a lateral femoral condyle surface having a curved contour and spaced apart from the medial femoral condyle. The rasping side may include a plurality of surfaces including an anterior rasping surface having a first set of rasping teeth, a medial posterior rasping surface having a second set of rasping teeth, and a lateral posterior rasping surface having a third set of rasping teeth. The impactor adaptor may include a first end configured to be coupled to an orthopaedic impactor and a second end, opposite the first end, having a connector configured to selectively couple to the articular side of the femoral finishing rasp.

In some embodiments, the first set of rasping teeth and the second set of rasping teeth are arranged or oriented to face in the proximal direction away from the body of the femoral finishing rasp. In such embodiments, the first and second set of rasping teeth may be configured to rasp a bone of a patient in a proximal-distal direction. In other embodiments, the first set of rasping teeth and the second set of rasping teeth are arranged or oriented to face in the distal direction toward the body of body of the femoral finishing rasp.

In some embodiments, the articular side of the femoral finishing rasp may define a femoral trial surface. Additionally, in some embodiments, the impactor adaptor may include a shank and a head separate from the shank. The shank may include the first end configured to be coupled to the orthopaedic impactor, and the head may include the second end having the connector configured to selectively couple to the articular side of the femoral finishing rasp. In such embodiments, the impactor adaptor may further include a securing device, the head may include a passageway defined therethrough, and the shank may include a mounting end, opposite the first end, having an aperture defined therein. The securing device may be configured to be received through the passageway of the head and into the aperture of the mounting end of the shank to secure the head to the shank.

Additionally, in some embodiments, the articular side of the body of the femoral finishing rasp may include a pair of apertures defined therein. In such embodiments, the connector of the impactor adaptor may include a pair of posts extending outwardly from the head, and each post may be configured to be received in a corresponding aperture of the pair of apertures of the articular side of the femoral finishing rasp when the impactor adaptor is coupled to the femoral finishing rasp. In some embodiments, each post of the pair of posts may include a ball detent configured to secure the impactor adaptor to the femoral finishing rasp when the posts are received in the apertures of the articular side of the femoral finishing rasp.

According to a further aspect, a method for performing an orthopaedic surgical procedure may include surgically preparing a distal end of a patient's femur, including performing at least one bone cut on the patient's femur, and assembling a femoral finishing rasp assembly by attaching an impactor adaptor to an exterior side of a femoral finishing rasp. The femoral finishing rasp may include a rasping side opposite the exterior side, and the rasping side of the femoral finishing rasp may include an anterior surface having a first set of rasping teeth and a distal surface having a second set of rasping teeth. The method may also include coupling the impactor adaptor to an orthopaedic impactor and rasping the distal end of the patient's femur using the orthopaedic impactor and femoral finishing rasp assembly. In some embodiments, rasping the distal end of the patient's femur may include rasping the distal end of the patient's femur in a proximal-distal direction.

In some embodiments, attaching the impactor adaptor to the exterior side of the femoral finishing rasp may include operating a pair of tabs of a connector of the impactor adaptor to position a catch of each tab into an aperture of a corresponding bracket of a connector of the femoral finishing rasp. Additionally, in some embodiments, the exterior side of the femoral finishing rasp may include a medial femoral condyle surface having a curved contour and a lateral femoral condyle surface having a curved contour and spaced apart from the medial femoral condyle. In such embodiments, the method may further include using the femoral finishing rasp as a femoral trial during the orthopaedic surgical procedure.

BRIEF DESCRIPTION OF THE DRAWINGS

The detailed description particularly refers to the following figures, in which.

DETAILED DESCRIPTION OF THE DRAWINGS

Figure 1:
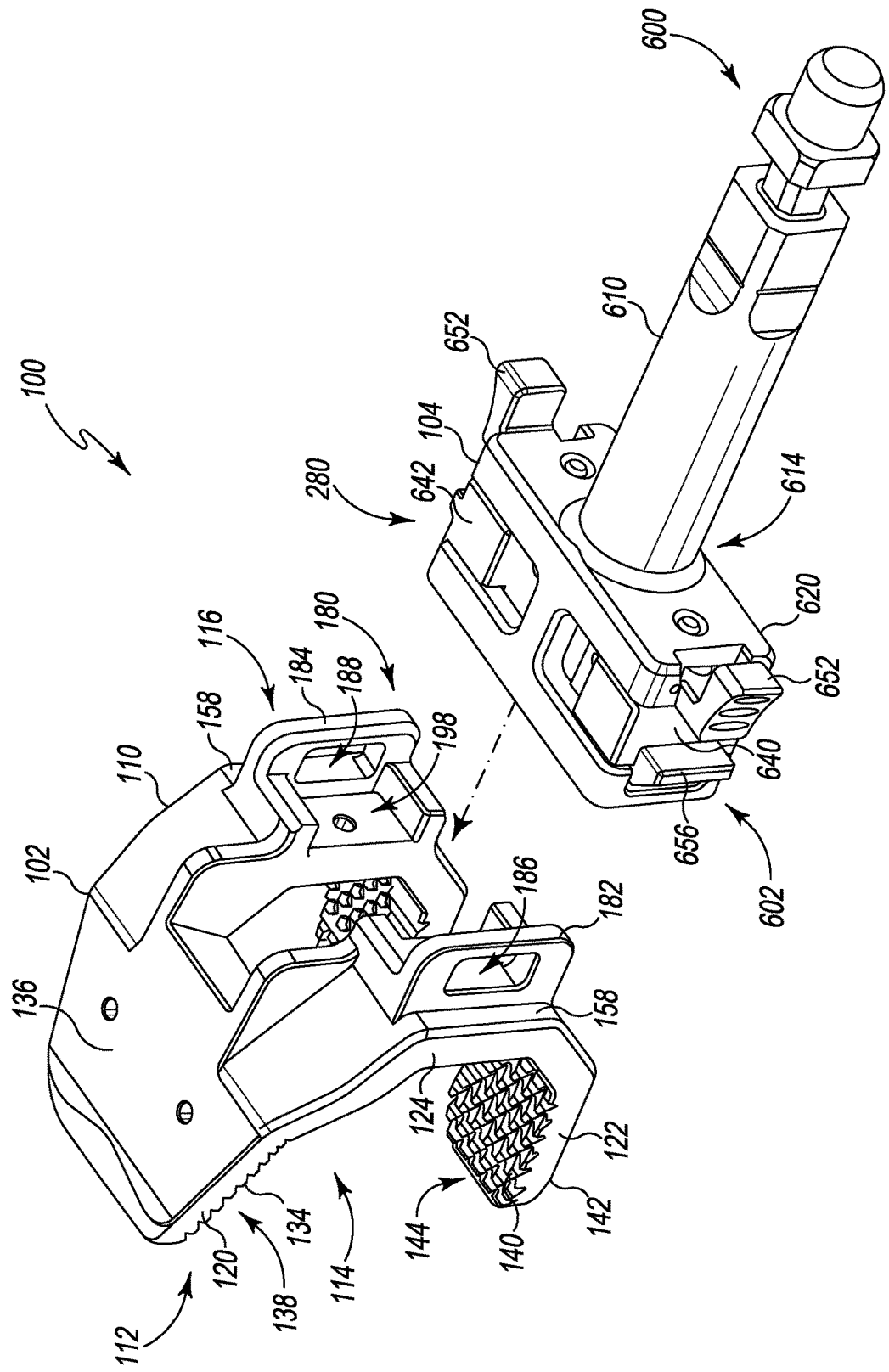
FIG. 1 is a partially exploded, distal perspective view of an embodiment of a femoral finishing rasp assembly including a femoral finishing rasp and an impactor adaptor.

While the concepts of the present disclosure are susceptible to various modifications and alternative forms, specific illustrative embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and/or surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIGS. 1-5, an illustrative femoral finishing rasp assembly 100 includes a femoral finishing rasp 102 and an impactor adaptor 104 configured to be coupled to the femoral finishing rasp 102. To do so, as described in more detail below, a connector 180 of the impactor adaptor 104 is coupled to or otherwise mated with a corresponding connector 280 of the femoral finishing rasp 102. Once assembled in this manner, the impactor adaptor 104 may be coupled to an orthopaedic impactor and subsequently used to rasp the distal end of a patent's surgically prepared femur. For example, after the patient's femur is initially surgically prepared by performing a number of bone cuts (e.g., a distal cut, an anterior cut, a posterior cut, and chamfer cuts), an orthopaedic surgeon may utilize the femoral finishing rasp assembly 100 to rasp or reshape the resected femoral bone to a desired size and/or shape so as to fit a selected femoral prosthesis.

The femoral finishing rasp 102 may be made from any suitable material having enough rigidity to successfully rasp a patient's bone. For example, the femoral finishing rasp 102 may be made from a metal material, such as steel or titanium. Alternatively, in some embodiments, the femoral finishing rasp 102 is embodied as a single-use orthopaedic instrument and may be formed form a plastic or ceramic material.

Figure 3:
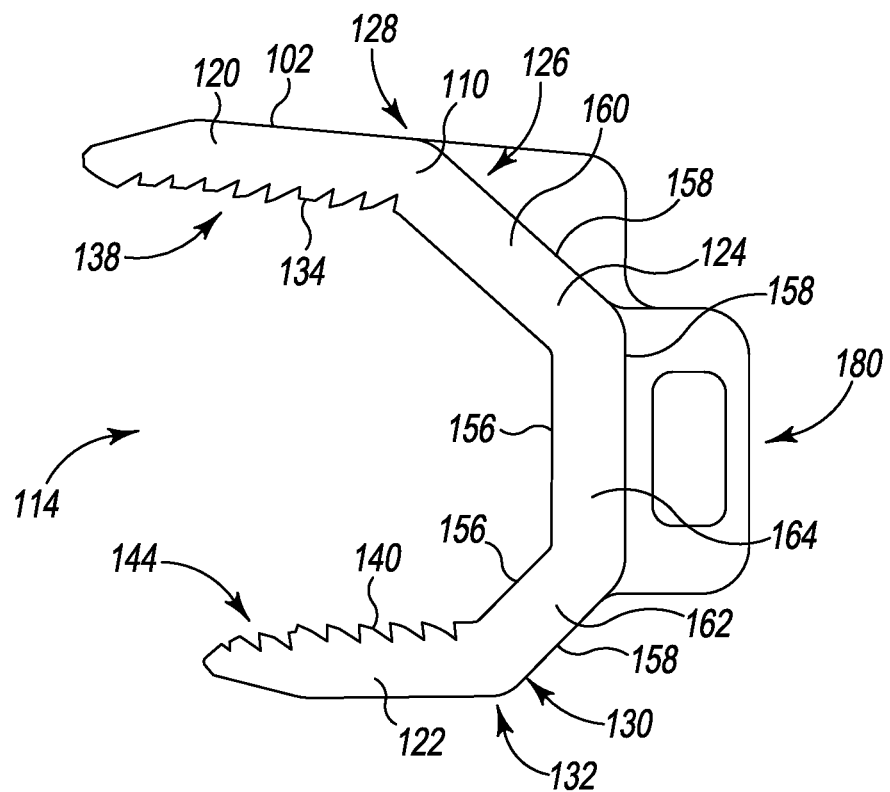
FIG. 3 is a side elevation view of the femoral finishing rasp of FIG. 2.

The illustrative femoral finishing rasp 102 includes a body 110 having an interior or rasping side 112 that defines an interior cavity 114 sized to receive a distal end of a patient's surgically-prepared femur and an exterior or mounting side 116 opposite the interior side 112. The body 110 includes an anterior wall 120, a posterior wall 122, and a distal wall 124 coupled to the anterior wall 120 and that posterior wall 122. That is, as best shown in FIG. 3, the distal wall 124 includes an anterior end 126 coupled to a distal end 128 of the anterior wall 120 and a posterior end 130 coupled to a distal end 132 of the posterior wall 122. In the illustrative embodiment, the body 110 of the femoral finishing rasp 102 is of a unitary construction, but may be formed as a multi-part component in other embodiments. For example, the anterior wall 120, posterior wall 122, and distal wall 124 may be separable from each other in such embodiments).

Figure 5:
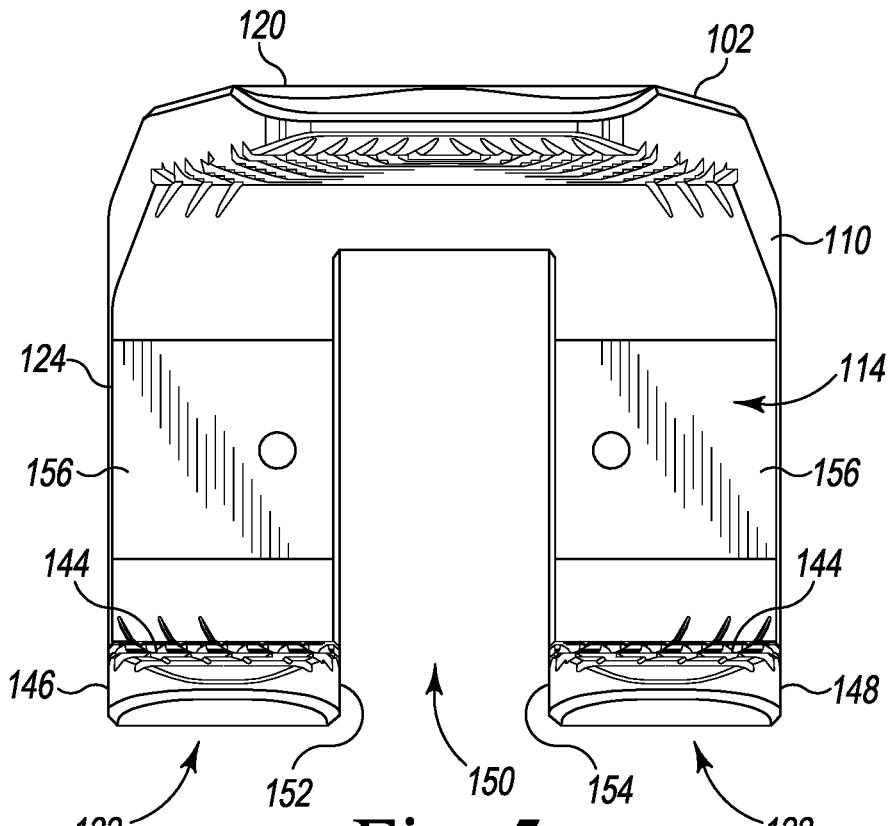
FIG. 5 is a proximal, interior elevation view of the femoral finishing rasp of FIG. 2.

The anterior wall 120 includes a femur-facing, interior surface 134 and an exterior surface 136, opposite the interior surface 134. The interior surface 134 of the anterior wall 120 faces the interior cavity 114 and includes a set of anterior rasping teeth 138. Similarly, the posterior wall 122 includes a femur-facing, interior surface 140 and an exterior surface 142, opposite the interior surface 140. The interior surface 140 of the posterior wall 122 also faces the interior cavity 114 and includes a set of posterior rasping teeth 144. In the illustrative embodiment, as best shown in FIG. 5, the posterior wall 122 is embodied as a medial posterior wall 146 and a lateral posterior wall 148 spaced apart from the medial posterior wall 146 by an aperture 150, each having a respective set of posterior rasping teeth 144. That is, the posterior wall 122 may include inner sidewalls 152, 154 that define the aperture 150 such that the posterior wall 122 include "condyle-like" medial and lateral posterior walls 146, 148. However, in other embodiments, the posterior wall 122 may be solid in the medial-to-lateral direction and devoid of the aperture 150.

In the illustrative embodiment, the rasping teeth 138 of the interior surface 134 of the anterior wall 120 and the rasping teeth 144 of the interior surface 140 of the posterior wall 122 are oriented to face in the proximal direction (i.e., toward the patient's bone) to facilitate a reciprocating rasping motion provided by an orthopaedic impactor. That is, as described below in regard to FIG. 10, the rasping teeth 138, 144 of the femoral finishing rasp 102 are arranged so as to rasp the distal end of the patient's surgically-prepared femur in a proximal-distal direction. In other embodiments, the rasping teeth 138, 144 may be arranged so as to face in the distal direction.

Similar to the anterior wall 120 and the posterior wall 122, the distal wall 124 includes a femur-facing, interior surface 156 facing the interior cavity 114 and an exterior surface 158, opposite the interior surface 156. However, unlike the anterior wall 120 and the posterior wall 122, the interior surface 156 of the distal wall 124 is devoid of rasping teeth in the illustrative embodiment. As shown in FIG. 3, the illustrative distal wall 124 includes an anterior chamfer wall 160 and a posterior chamfer wall 162, each of which is angled inwardly from a distal wall section 164. However, in other embodiments, the distal wall 124 may be substantially planar such that the body 110 of the femoral finishing rasp 102 has a substantially rectangular side profile.

Figure 4:
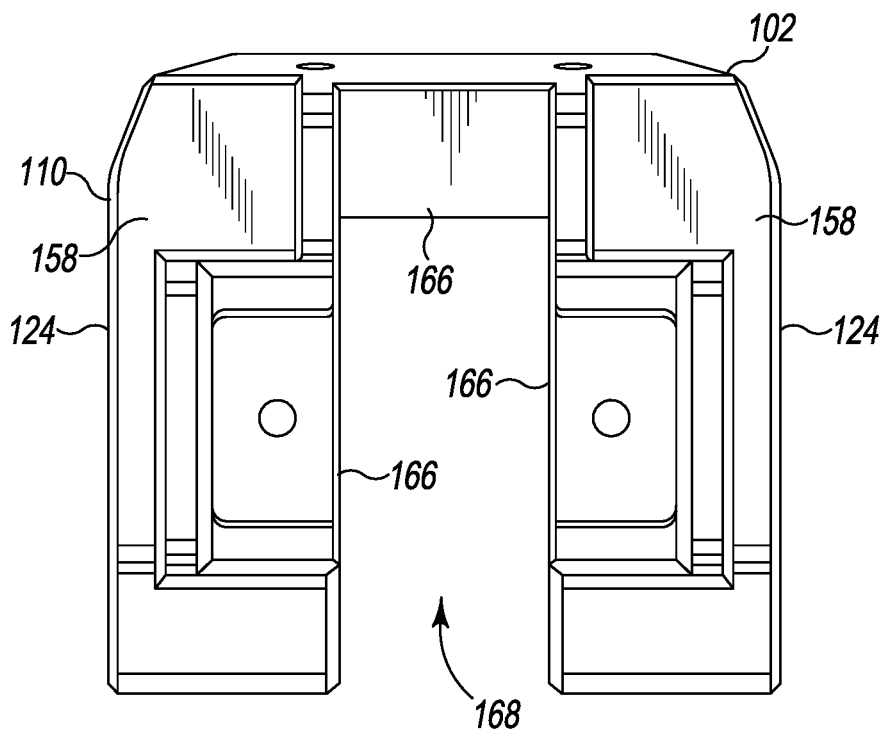
FIG. 4 is a distal, exterior elevation view of the femoral finishing rasp of FIG. 2.

As best shown in FIGS. 4 and 5, the distal wall 124 of the illustrative femoral finishing rasp 102 includes a number of inner walls 166 that cooperate to define an aperture 168 that extends through the distal wall 124. In some embodiments, one or more of the inner walls 166 may be embodied as a cutting guide. For example, the inner walls 166 may cooperate to define a posterior-stabilized trochlear box-cutting guide to facilitate the establishment of a trochlear box cut on the distal end of the patient's femur in some orthopaedic surgical procedures. In the illustrative embodiment, the aperture 168 is in fluid communication with the aperture 150 of the posterior wall 122 (see, e.g., FIG. 2); however, in other embodiment (e.g., those in which the posterior wall 122 is devoid of the aperture 150), the aperture 168 may be "closed" so as to form a passageway through the distal wall 124.

Figure 2:
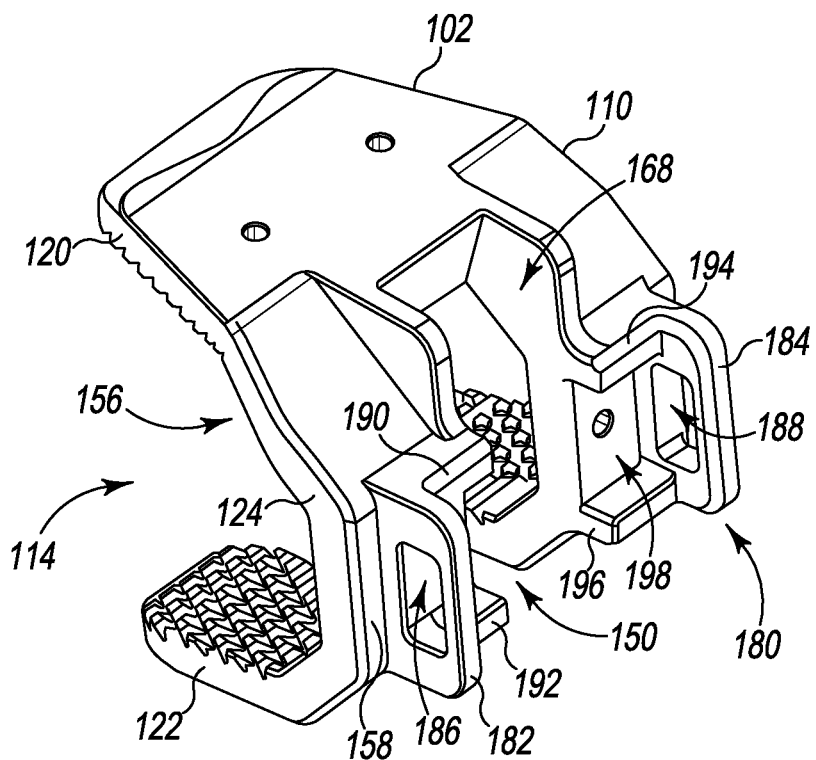
FIG. 2 is a distal perspective view of the femoral finishing rasp of the femoral finishing rasp assembly of FIG. 1.

As discussed above, the body 110 of the femoral finishing rasp 102 includes the connector 180, which extends from or is otherwise attached to the exterior surface 158 of the distal wall 124 of the body 110. The connector 180 of the femoral finishing rasp 102 is configured to mate with the connector 280 of the impactor adaptor 104. As best shown in FIG. 2, the illustrative connector 180 is embodied as or otherwise includes a medial bracket 182 and a lateral bracket 184, each of which is laterally spaced from the other. In embodiments, in which the distal wall 124 includes the aperture 168, the aperture 168 is located between the brackets 182, 184 as shown in FIG. 2. Each of the brackets 182, 184 extends distally from the exterior surface 158 of the distal wall 124 and is embodied as a "loop-like" bracket having an aperture, 186, 188, respectively, defined therethough. The apertures 186, 188 are coaxial or otherwise aligned with each other as best shown in FIGS. 1, 2, and 3. In some embodiments, as shown best in FIG. 2, the connector 180 of the of the femoral finishing rasp 102 may include a number of sidewalls, including a medial-anterior sidewall 190, a medial-posterior sidewall 192, a lateral-anterior sidewall 194, and a lateral-posterior sidewall 196, each of which extends distally from the distal wall 124 of the body 110. Illustratively, the sidewalls 190, 192, 194, 196 extend a smaller distance from the distal wall 124 relative to the brackets 182, 184 and cooperate with the brackets 182, 184 to define a recess 198 configured (e.g., shaped and sized) to receive a portion of the impactor adaptor 104 as discussed in more detail below.

Referring now to FIGS. 1 and 6-9, the impactor adaptor 104 includes a mounting end 600 configured (e.g., shaped and sized) to couple to a manual or automated orthopaedic impactor and a connector end 602, opposite the mounting end 600. The connector end 602 includes the connector 280, which is configured to couple or mate with the connector 180 of the femoral finishing rasp 102 as described in more detail below. In the illustrative embodiment of FIGS. 1-9, the impactor adaptor 104 includes an elongated body 610, which includes the mounting end 600 and another end 614, opposite the mounting end 600, coupled to the connector 280.

Figure 6:
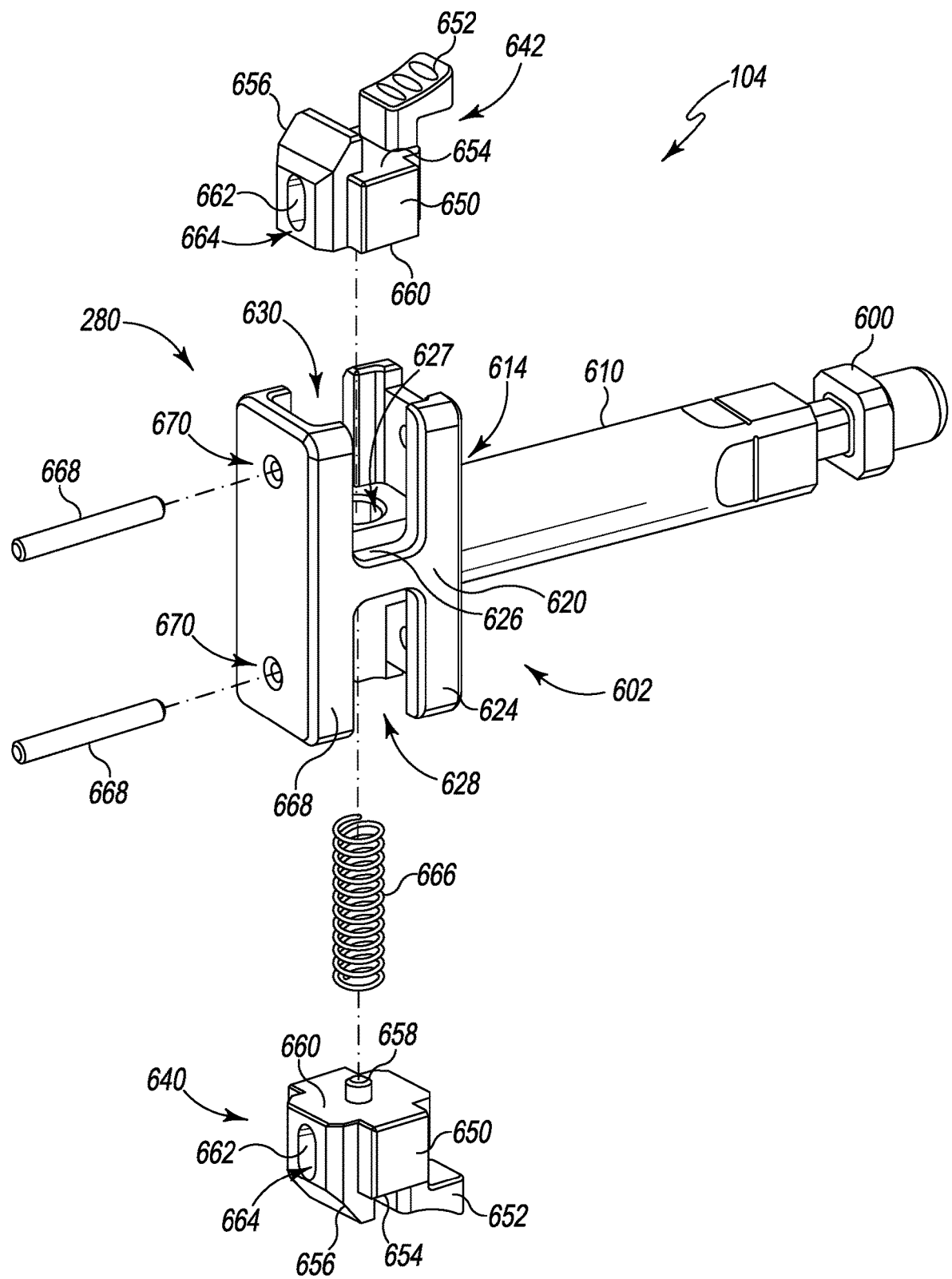
FIG. 6 is an exploded perspective view of the impactor adaptor of the femoral finishing rasp assembly of FIG. 1.
Figure 7:
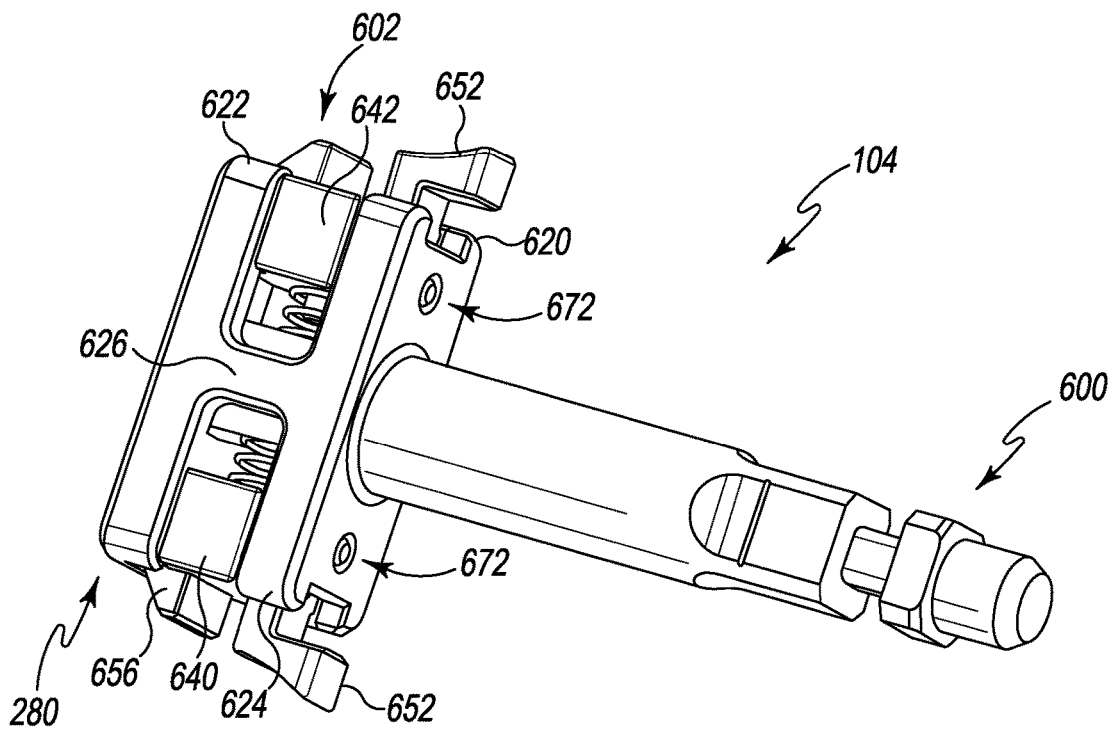
FIG. 7 is a distal perspective view of the impactor adaptor of FIG. 6.
Figure 8:
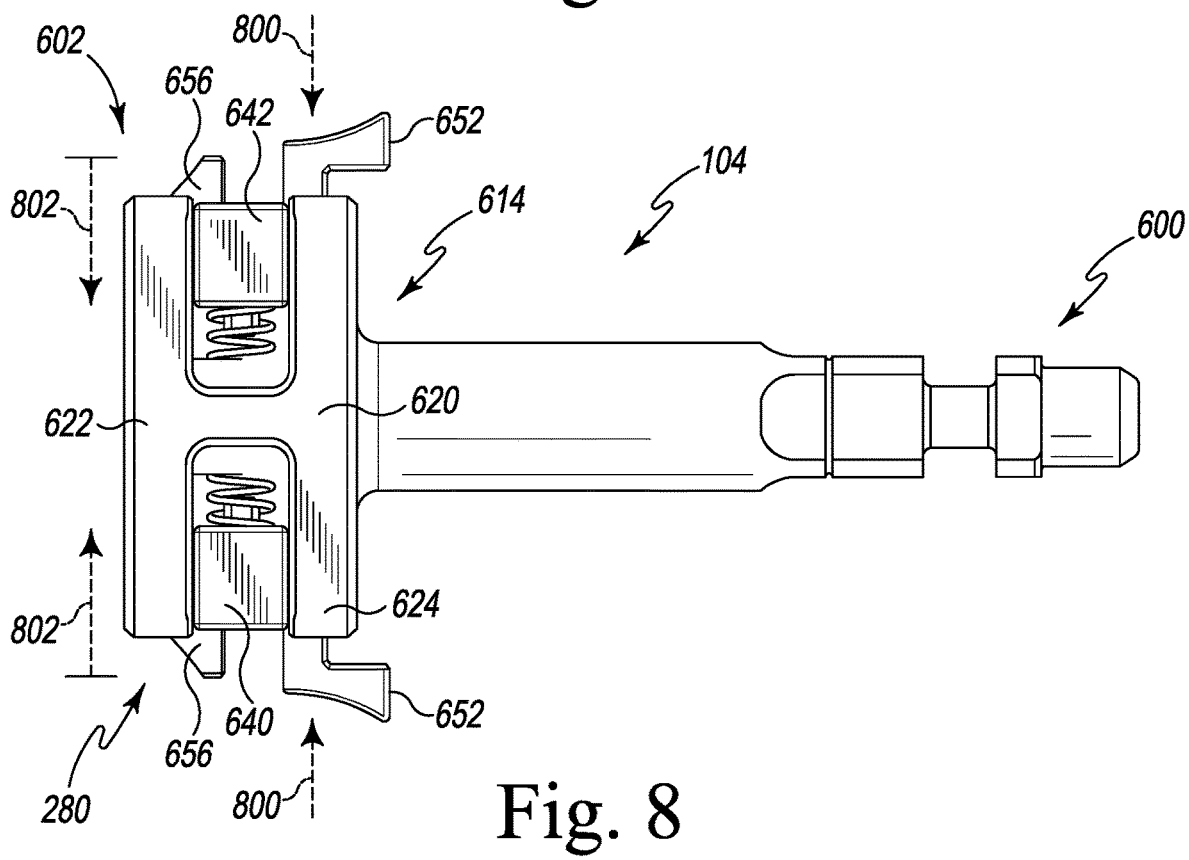
FIG. 8 is a side elevation view of the impactor adaptor of FIG. 6.

As shown best in FIGS. 6-8, the connector 280 of the impactor adaptor 104 includes a connector body 620 having a rectangular head 622 and a rectangular base 624 coupled to, and distally separated from, each other by a center wall 626. Illustratively, the center wall 626 includes an inner surface that defines a passageway 627 through the center wall 626 (see FIG. 6).

The head 622 and the base 624 cooperate to define a medial track 628 on one side of the center wall 626 and a lateral track 630. The connector 280 includes a medial tab 640 received in the medial track 628 and a lateral tab 642 received in the lateral track 630. Each of the tabs 640, 642 includes a body 650 having a handle 652 extending away from an outward side 654 of the body 650 and a catch 656 also extending away from the outward side 654 of the body 650. Additionally, each of the tabs 640, 642 includes nub 658 (see FIG. 6) that extends away from an inward side 660 of the corresponding tab 640, 642. Furthermore, each of the illustrative tabs 640, 642 also includes an inner surface 662 that defines a passageway 664 through the corresponding body 650.

The tabs 640, 642 are biased away from each other (i.e., outwardly from the center wall 626) via a biasing member, illustratively embodied as a spring 666. The spring 666 is received in the passageway 627 of the center wall 626 and coupled to each of the tabs 640, 642 via the respective nub 658. That is, each of the nubs 658 of the tabs 640, 642 is received in a corresponding end of the spring 666 such that the spring 666 can be compressed by sliding the tabs 640, 642 inwardly along their corresponding track 628, 630 as discussed in more detail below. Each of the tabs 640, 642 is secured in the corresponding track 628, 630 via a corresponding securing pin 668, which is received through a corresponding passageway 670 defined through the head 622 (see FIG. 6), through the passageway 644 of the corresponding tab 640, 642, and into a corresponding passageway 672 define through the base 624 (see FIG. 7) of the connector body 620.

Figure 9:
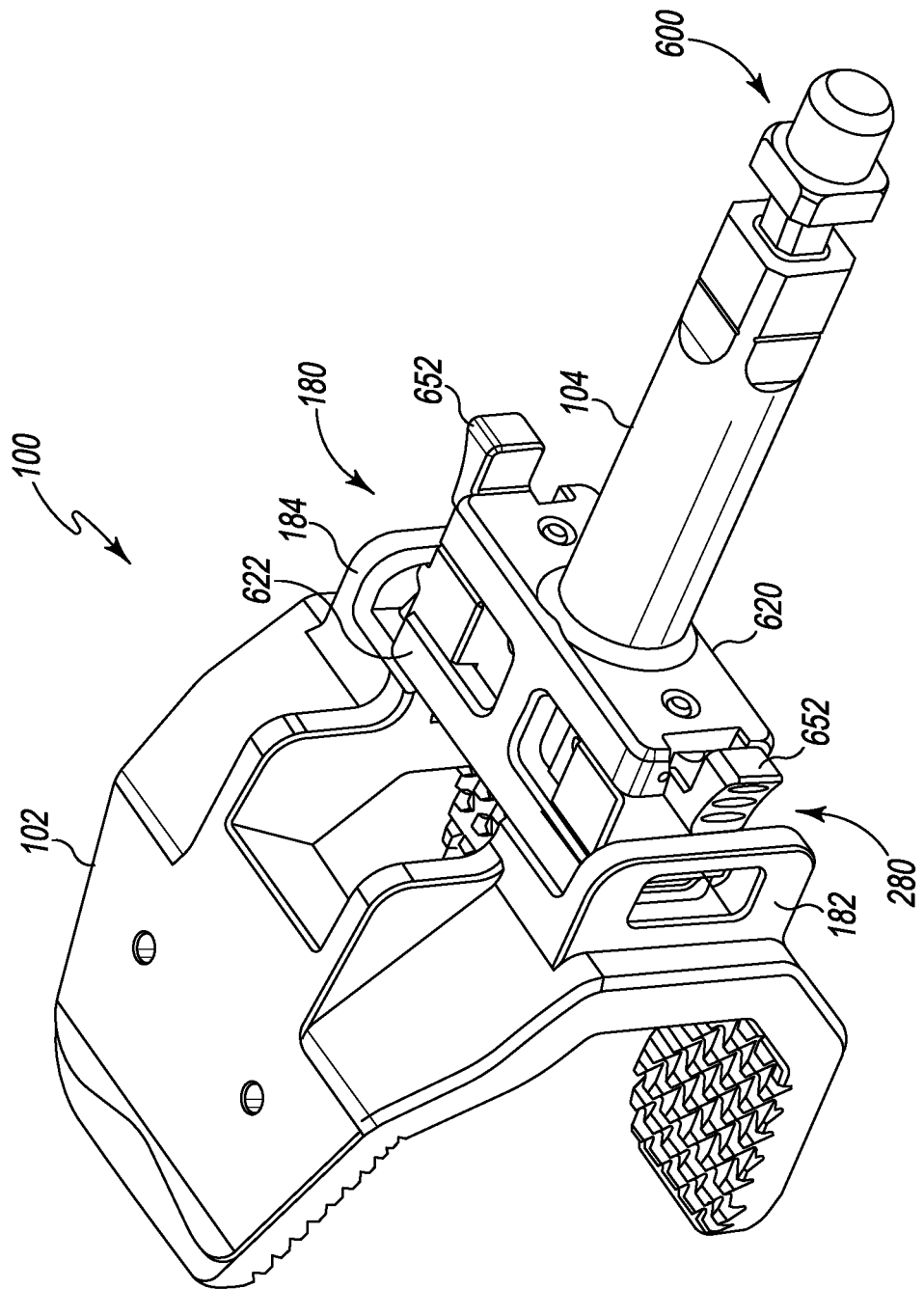
FIG. 9 is a distal perspective view of the femoral finishing rasp assembly of FIG. 1 having the impactor adaptor coupled to the femoral finishing rasp.

As discussed above, the impactor adaptor 104 may be coupled to the femoral finishing rasp 102 by coupling the connector 280 of the impactor adaptor 104 to the connector 180 of the femoral finishing rasp 102. To do so in the illustrative embodiment, as shown in FIGS. 8 and 9, an orthopedic surgeon (or other user) may depress the handles 652 of the tabs 640, 642 toward each other as indicated by arrows 800, which compresses the spring 666 and causes the tabs 640, 642 to move toward each other in their corresponding tracks 628, 630. As the tabs 640, 642 are moved toward each other, their corresponding catches 656 retract into the connector body 620 as indicated by arrows 802. As such, as shown in FIG. 9, with the catches 656 of the tabs 640, 642 retracted into the connector body 620, the head 622 of the connector body 620 may be inserted between the medial and lateral brackets 182, 184 and into the recess 198 of the connector 180 of the femoral finishing rasp 102. When the handles 652 of the tabs 640, 642 are subsequently released while the connector 280 is so positioned, the biasing force of the spring 666 extends the catches 656 outwardly from the connector body 620 and into the aperture 186, 188 of the corresponding bracket 182, 184 of the connector 180. In this way, the impactor adaptor 104 may be selectively coupled and decoupled from the femoral finishing rasp 102.

Figure 10:
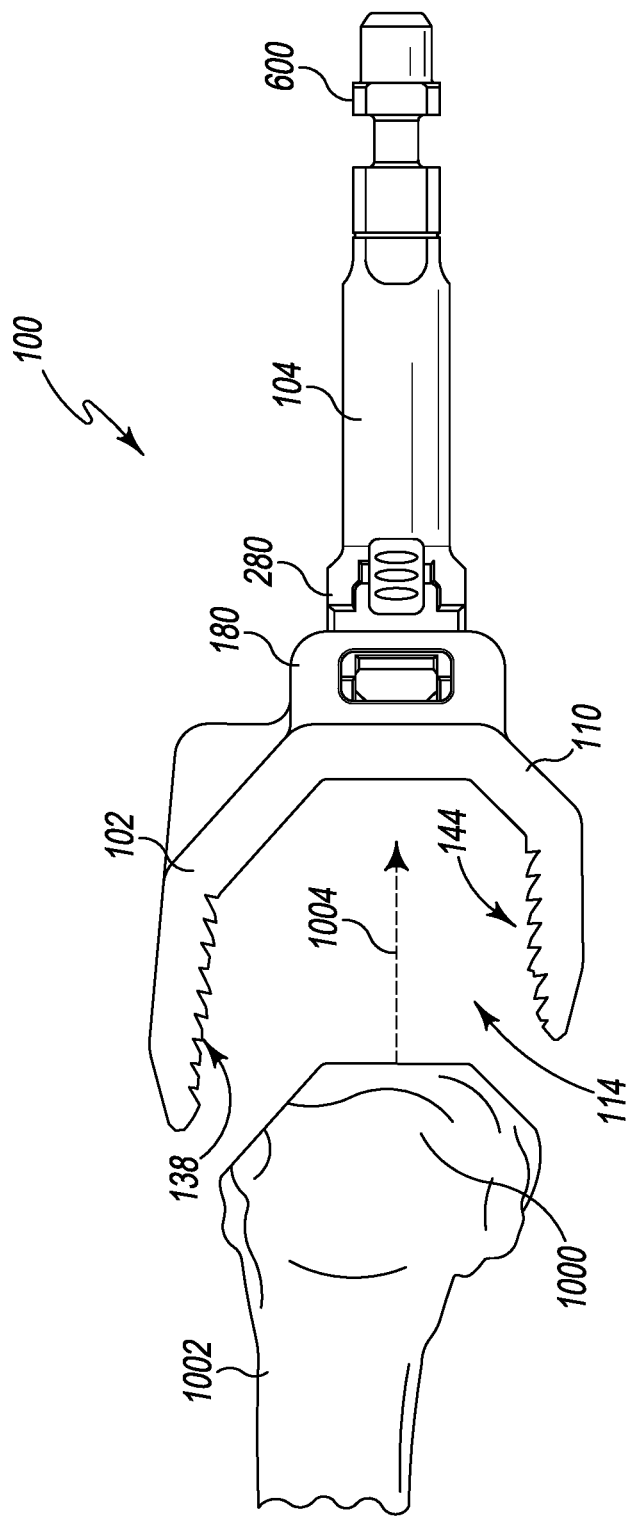
FIG. 10 is a side elevation view of the femoral finishing rasp assembly of FIG. 9 in the process of rasping a distal end of a patient's femur.

As shown in FIG. 10, with the impactor adaptor 104 coupled to the femoral finishing rasp 102 to form the femoral finishing rasp assembly 100, the femoral finishing rasp assembly 100 may be used to rasp a surgically-prepared distal end 1000 of a patient's femur 1002. To do so, femoral finishing rasp is inserted over the patient's femur 1002 such that the distal end 1000 of the femur 1002 is received in the interior cavity 114 of the body 110 of the femoral finishing rasp 102 as indicated by arrow 1004. As discussed above, the rasping teeth 138, 144 of the femoral finishing rasp 102 are arranged to face the proximal direction (i.e., toward the patient's femur 1002) and rasp the patient's femur 1002 in a proximal-distal direction.

Figure 11:
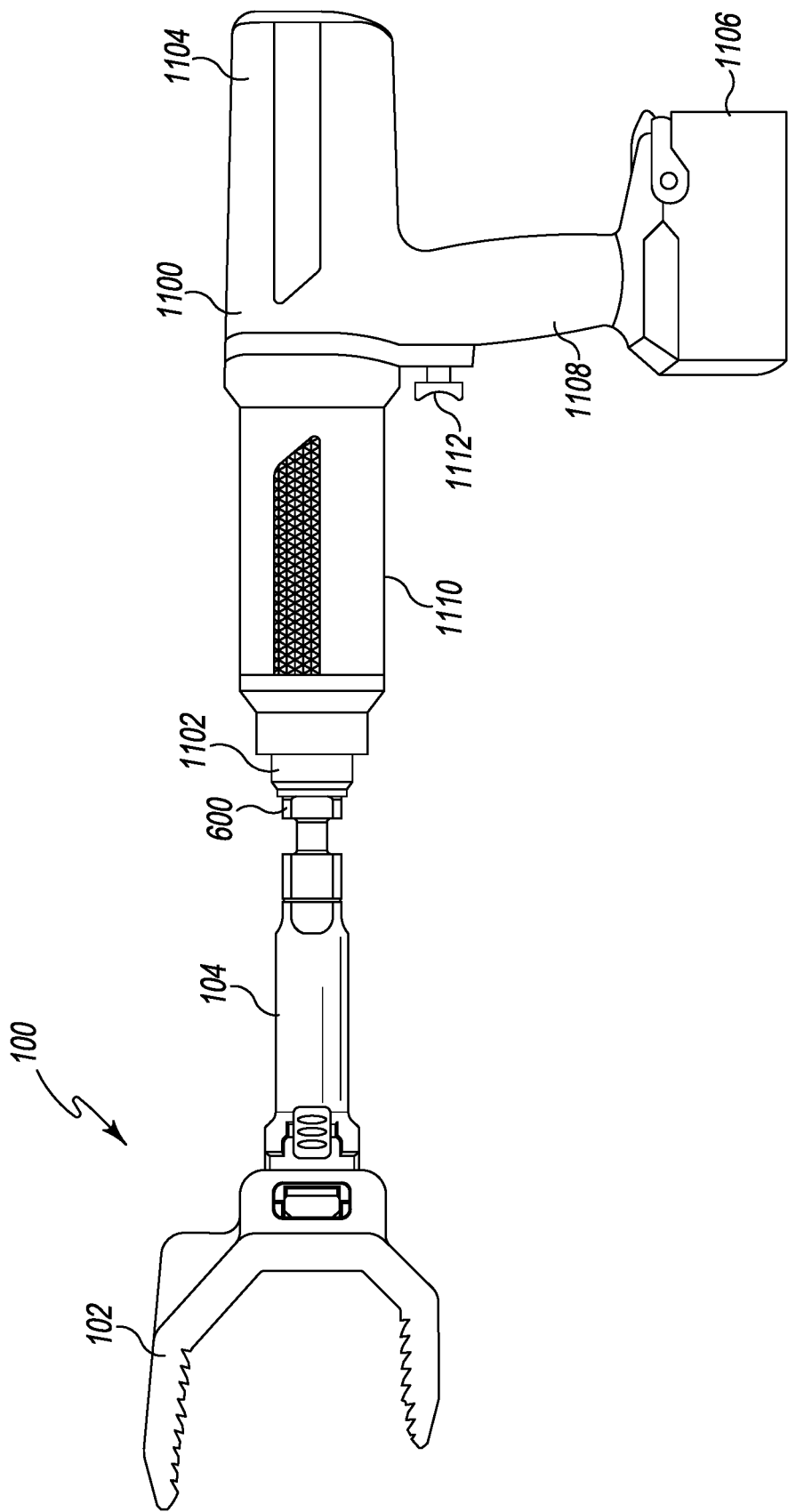
FIG. 11 is a side elevation view of the femoral finishing rasp assembly of FIG. 9 coupled to an automated impactor.

As discussed above, the impactor adaptor 104 of the femoral finishing rasp assembly 100 includes the mounting end 600 configured to be coupled to an orthopaedic impactor to facilitate the rasping of the distal end 1000 of the patient's femur 1002. For example, as shown in FIG. 11, the femoral finishing rasp assembly 100 may be coupled to an automated impactor 1100. To do so, the mounting end 600 may be coupled to a chuck 1102 of the automated impactor 1100 and secured therein by operation of the chuck 1102. Once so coupled, the orthopedic surgeon may operate the automated impactor 1100 in a typical manner to cause actuation of the femoral finishing rasp 102.

The automated impactor 1100 may be embodied as any type of automated impactor having a chuck capable of coupling with the mounting end 600 of the impactor adaptor 104. For example, in some embodiments, the automated impactor 1100 may be embodied as a Kincise™ surgical automated system component commercially available from DePuy Synthes of Warsaw, Indiana. In the illustrative embodiment, the automated surgical impactor 1100 includes an impactor body 1104 having the chuck 1102 and a battery pack 1106. Electrical drive components are housed within the impactor body 1104. The impactor body 1104 further illustratively includes a primary handgrip 1108, a secondary handgrip 1110, and a trigger 1112.

Figure 12:
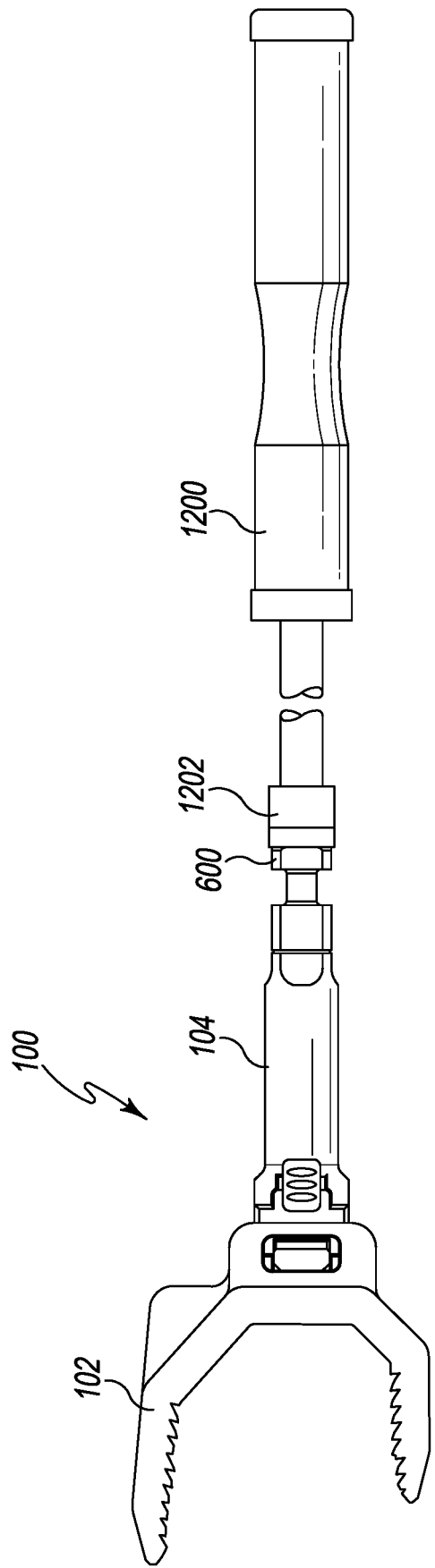
FIG. 12 is a side elevation view of the femoral finishing rasp assembly of FIG. 9 coupled to a manual impactor.

Alternatively, as shown in FIG. 12, the femoral finishing rasp assembly 100 may be coupled to a manual orthopaedic impactor 1200. To do so, the mounting end 600 of the impactor adaptor 104 may be coupled to a chuck 1202 of the manual impactor 1200 and secured therein. Once so coupled, the orthopedic surgeon may utilize the manual impactor 1200 to rasp the distal end 1000 of the patient's femur 1002, similar to a typical manual rasp.

Referring now to FIG. 13-17, in another embodiment, the impactor adaptor 104 is configured to be secured to the femoral finishing rasp 102 via use of a securing device 1300, such as a bolt or screw. In such embodiments, the aperture 168 of the distal wall 124 is embodied as a passageway 1302 that extends though the distal wall 124. That is, the passageway 1302 includes an opening 1304 defined on the interior surface 156 and an opening 1306 defined on the exterior surface 158 of the distal wall 124. In such embodiments, the connector 180 of the femoral finishing rasp 102 includes a rim 1308 that encircles the passageway 1302 and extends distally away from the exterior surface 158 of the distal wall 124 to form a receptacle 1310. The connector 280 of the impactor adaptor 104 is embodied as a nub 1312 having a similar shape as to the receptacle 1310 and sized to be received in the receptacle 1310. That is, when the impactor adaptor 104 is coupled to the femoral finishing rasp 102 in the illustrative embodiment of FIGS. 13-17, the nub 1312 of the connector 280 of the impactor adaptor 104 is received in the receptacle 1310 of the connector 180 of the femoral finishing rasp 102.

Figure 13:
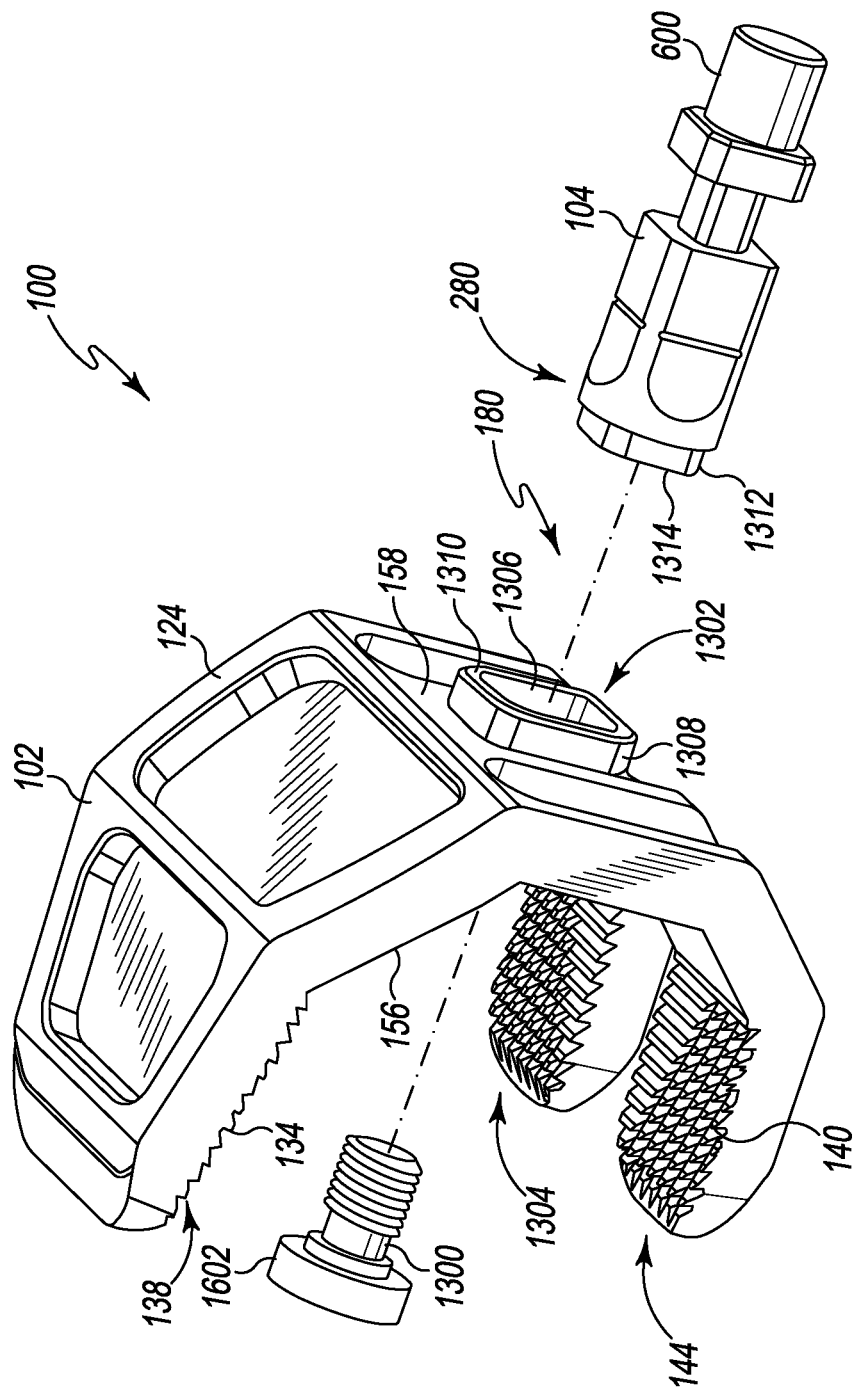
FIG. 13 is a partially exploded, distal perspective view of another embodiment of a femoral finishing rasp assembly including a femoral finishing rasp and an impactor adaptor.
Figure 14:
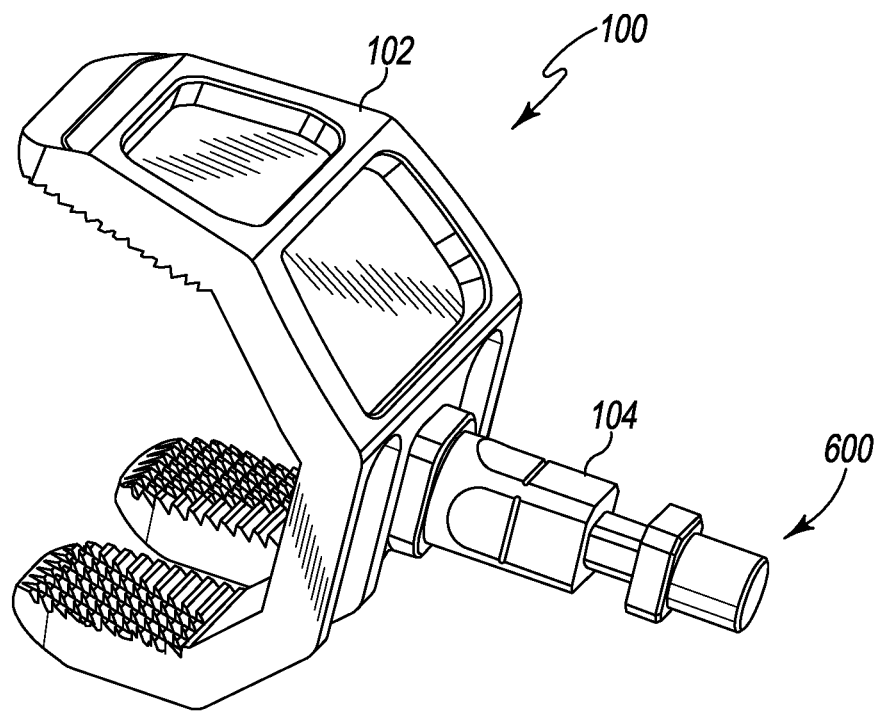
FIG. 14 is a distal perspective view of the femoral finishing rasp assembly of FIG. 13 having the impactor adaptor coupled to the femoral finishing rasp.
Figure 15:
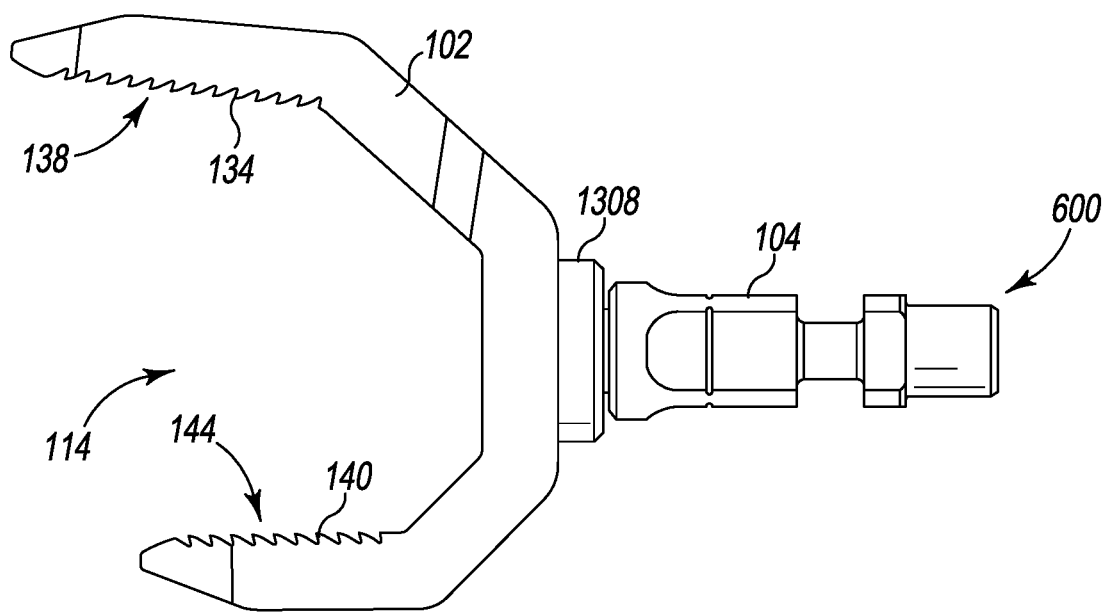
FIG. 15 is a side elevation view of the femoral finishing rasp assembly of FIG. 14.
Figure 16:
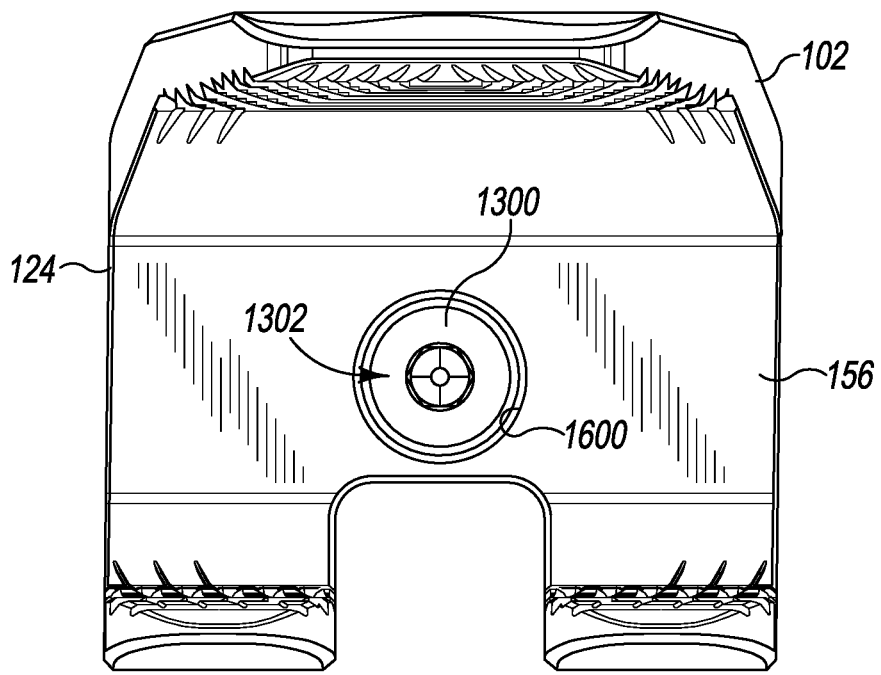
FIG. 16 is a proximal, interior elevation view of the femoral finishing rasp assembly of FIG. 14.
Figure 17:
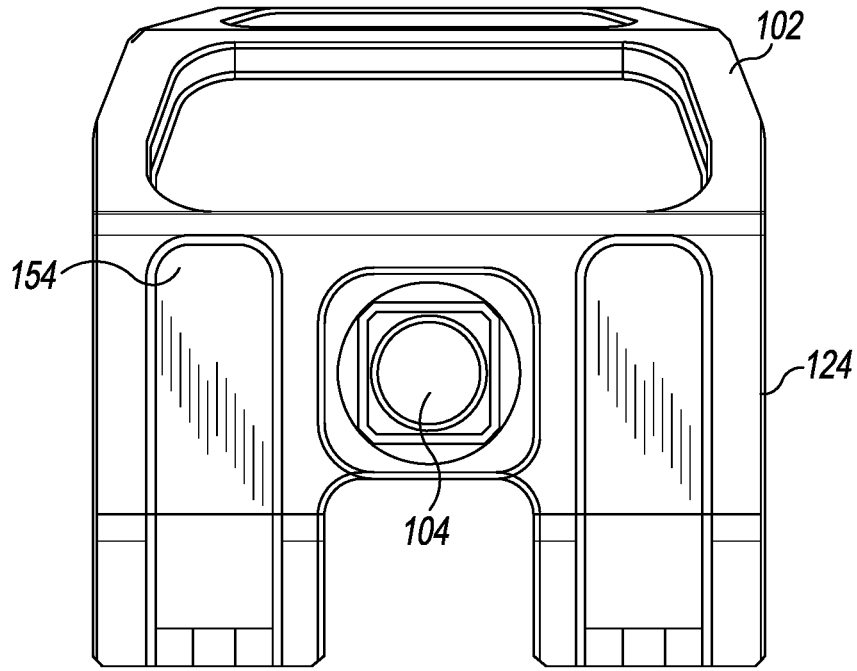
FIG. 17 is a distal, exterior elevation view of the femoral finishing rasp assembly of FIG. 14.

To facilitate securement of the impactor adaptor 104 to the femoral finishing rasp 102, the nub 1312 includes a threaded aperture (not shown) defined on a proximal wall 1314 of the nub 1312 and configured to receive the securing device 1300. That is, to secure impactor adaptor 104 to the femoral finishing rasp 102, the securing device 1300 is inserted through the passageway 1302 of the distal wall 124 of the body 110 of the femoral finishing rasp 102 and threaded into, or otherwise received in, the threaded aperture of the nub 1312 of the connector 180 of the impactor adaptor 104 as indicated in FIG. 13. Additionally, as best shown in FIG. 16, the interior surface of the distal wall 124 of the femoral finishing rasp 102 may include a recess 1600 surrounding the passageway 1302, which is sized to receive a head 1602 of the securing device 1300 (see FIG. 13) such that the securing device 1300 is relatively flush with the interior surface 156 of the distal wall 124 when the impactor adaptor 104 is secured to the illustrative femoral finishing rasp 102 of FIGS. 13-17.

It should be appreciated that the impactor adaptor 104 may be embodied as a universal impactor adaptor 104 configured to be used with different femoral finishing rasps 102. For example, in some embodiments, multiple femoral finishing rasps 102 of different sizes may be provided. In such embodiments, the orthopaedic surgeon may select the proper femoral finishing rasp 102 from the set of femoral finishing rasps 102 and couple the impactor adaptor 104 to the selected femoral finishing rasp 102, as discussed above.

Referring now to FIGS. 18-23, in another embodiment, the femoral finishing rasp 102 of the femoral finishing rasp assembly 100 may be embodied as a femoral trial finishing rasp 1802, and the impactor adaptor 104 may be embodied as a multi-piece impactor adaptor 1804. The femoral finishing rasp assembly 100 illustrated in and describe below in regard to FIGS. 18-23 has similar features to the femoral finishing rasp assemblies 100 discussed above and some description of those similar features are omitted below with the understanding the description provided above of such features may be equally applicable to the corresponding features of the femoral finishing rasp assembly 100 of FIG. 18-23.

Figure 18:
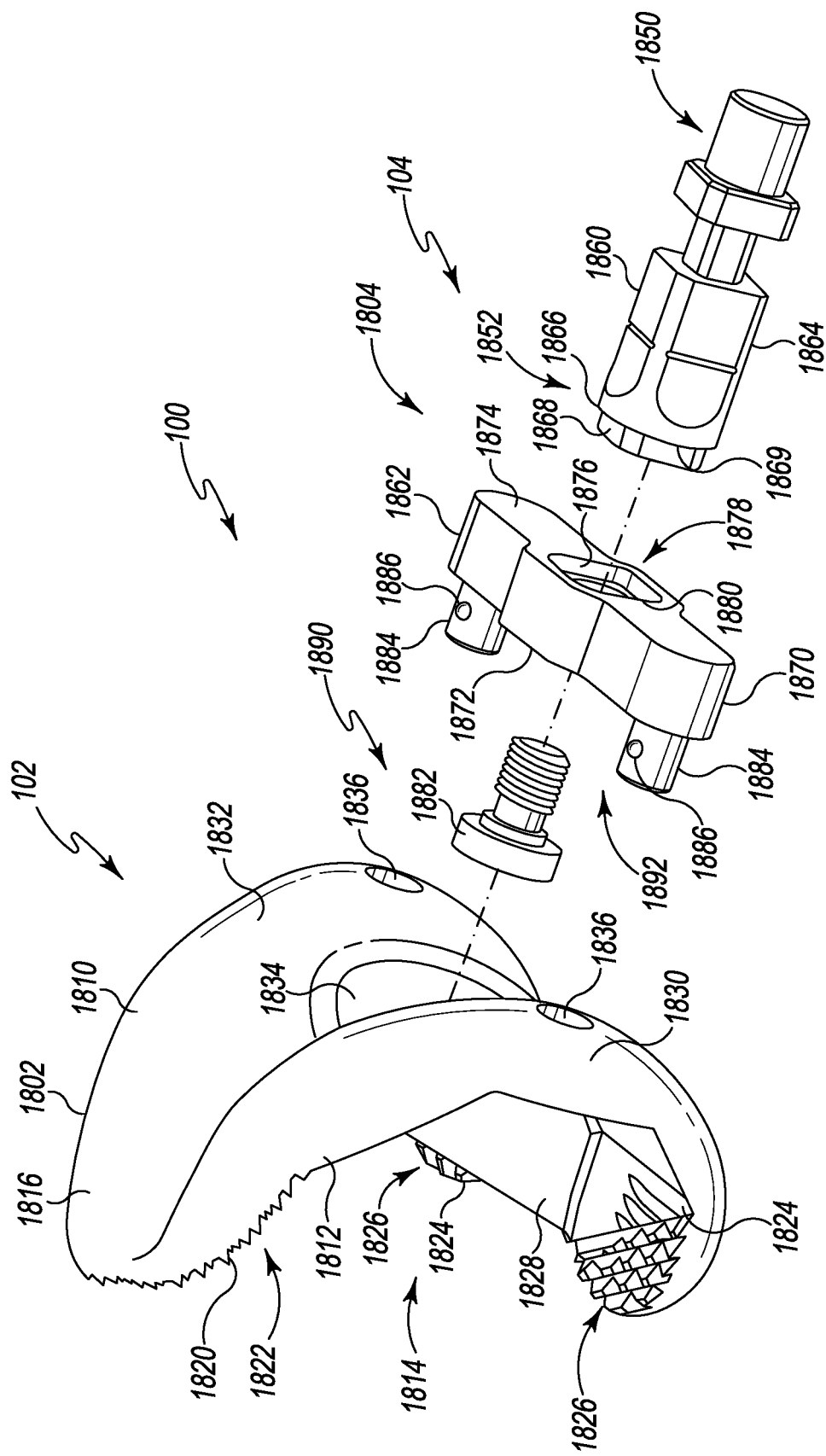
FIG. 18 is a partially exploded, distal perspective view of a further embodiment of a femoral finishing rasp assembly including a femoral trial finishing rasp and an impactor adaptor, with the impactor adaptor shown in an unassembled configuration.

As best illustrated in FIG. 18, the femoral trial finishing rasp 1802 includes a body 1810 having an interior or rasping side 1812 that defines an interior cavity 1814 sized to receive a distal end of a patient's surgically-prepared femur and an exterior or articular side 1816 opposite the rasping side 1812. Similar to the femoral finishing rasp 102 of FIGS. 1-2, the rasping side 1812 of the femoral trial finishing rasp 1802 includes an anterior, interior surface 1820 having a set of anterior rasping teeth 1822 and a pair of posterior, interior surfaces 1824 (e.g., medial and lateral posterior surfaces) spaced apart from each other by a trochlear box housing 1828 and having a respective set of posterior rasping teeth 1826.

Unlike the previously discussed femoral finishing rasps 102, however, femoral trial finishing rasp 1802 includes the articular side 1816, which illustratively includes a medial femoral condyle surface 1830 and a lateral condyle surface 1832 spaced apart from each other by an opening 1834 of the trochlear box housing 1828 defined in the articular side 1816. Each of the medial and lateral femoral condyle surfaces 1830, 1832 has a curved contour and is embodied as a femoral trial surface configured to articulate on a patient's natural or artificial tibial plateau.

The body 1810 of the femoral trial finishing rasp 1802 also includes a connector 1890 located on the articular side 1816 of the body 1810 and configured to couple with, or otherwise mate with, a corresponding connector 1892 of the impactor adaptor 1804. Illustratively, the connector 1890 is embodied as a pair of apertures 1836, each of which is defined in a respective one of the medial and lateral femoral condyles surfaces 1830, 1832 of the articular side 1816.

The illustrative multi-piece impactor adaptor 1804 includes a mounting end 1850 configured (e.g., shaped and sized) to couple to a manual or automated orthopaedic impactor and a connector end 1852, opposite the mounting end 1850. The connector end 1852 includes the connector 1892, which is configured to couple or mate with the connector 1890 of the femoral trial finishing rasp 1802 as described in more detail below.

As illustrated in FIG. 18, the illustrative impactor adaptor 1804 is a multi-piece adaptor including an elongated shank 1860 and a head 1862 separate from the shank 1860. The illustrative shank 1860 is substantially similar to the impactor adaptor 104 of FIGS. 13-17 and may be used with the femoral finishing rasp 102 described above, as well as the femoral trial finishing rasp 1802 of FIGS. 18-22. The shank 1860 includes an elongated shaft 1864 having the mounting end 1850 and a head end 1866 opposite the mounting end 1850. Similar to the impactor adaptor 104 of FIGS. 13-17, the head end 1866 includes a nub 1868 that extends outwardly from a proximal surface 1869 of the head end 1866. The nub 1868 includes a threaded aperture (not shown) defined therein.

The head 1862 of the illustrative impactor adaptor 1804 includes a body 1870 having a proximal side 1872 and a distal side 1874 opposite the proximal side 1872. The head 1862 also includes an inner wall 1876 that defines a passageway 1878 through the head 1862. The passageway 1878 includes an opening defined on the distal side 1874 of the head 1862 and which forms a receptacle 1880 configured to receive the nub 1868 of the elongated shank 1860 when the head 1862 is coupled to the shank 1860. To secure the head 1862 to the shank 1860 of the femoral trial finishing rasp 1802, a securing device 1882, such as a bolt or screw, may be interested through the passageway 1878 of the head 1862 and threaded into the threaded aperture of the nub 1868 of the elongated shank 1860 while the nub 1868 is received in the receptacle 1880 of the head 1862.

Figure 19:
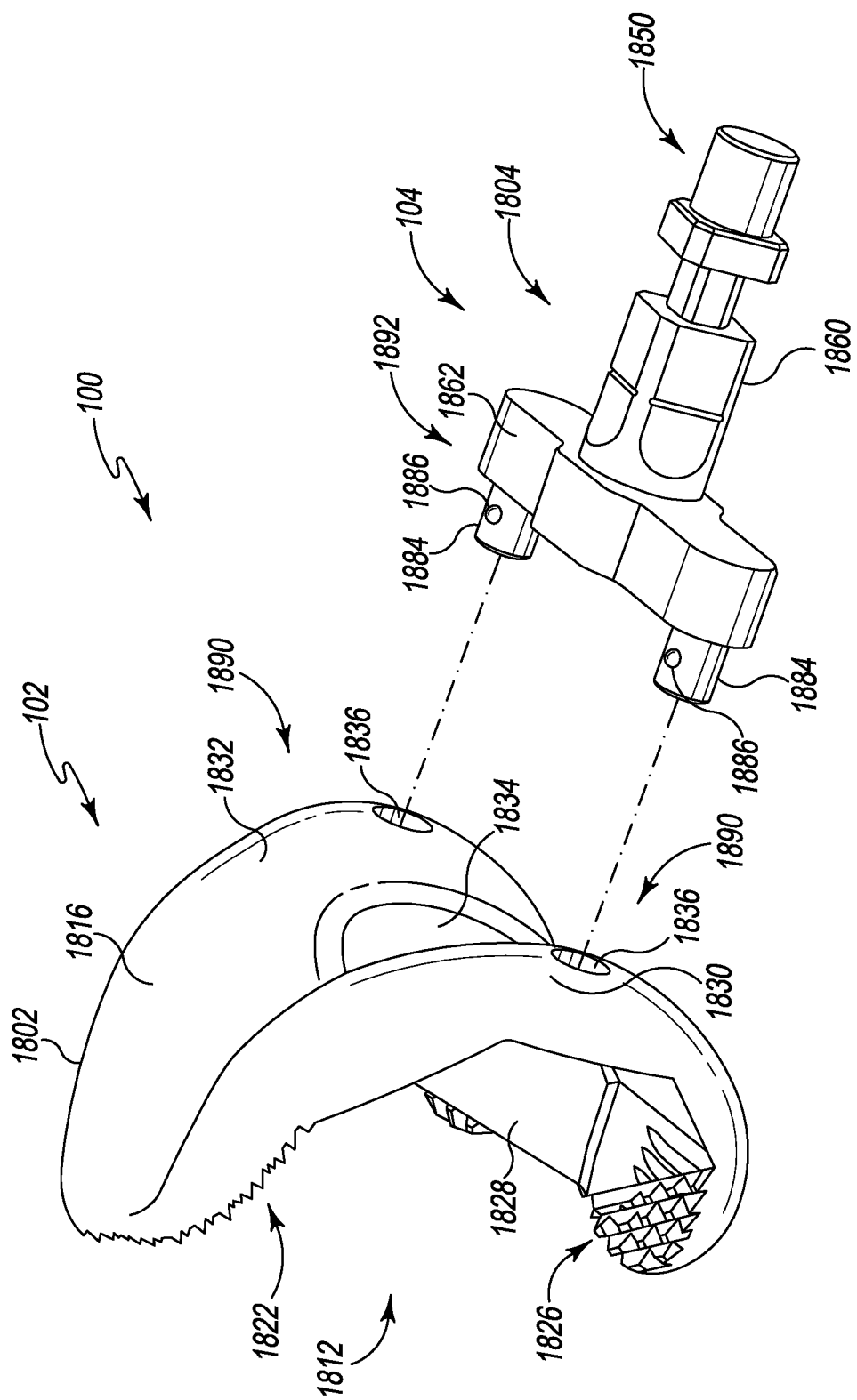
FIG. 19 is another partially exploded, distal perspective view of the femoral finishing rasp assembly of FIG. 18 having the impactor adaptor shown in an assembled configuration.
Figure 20:
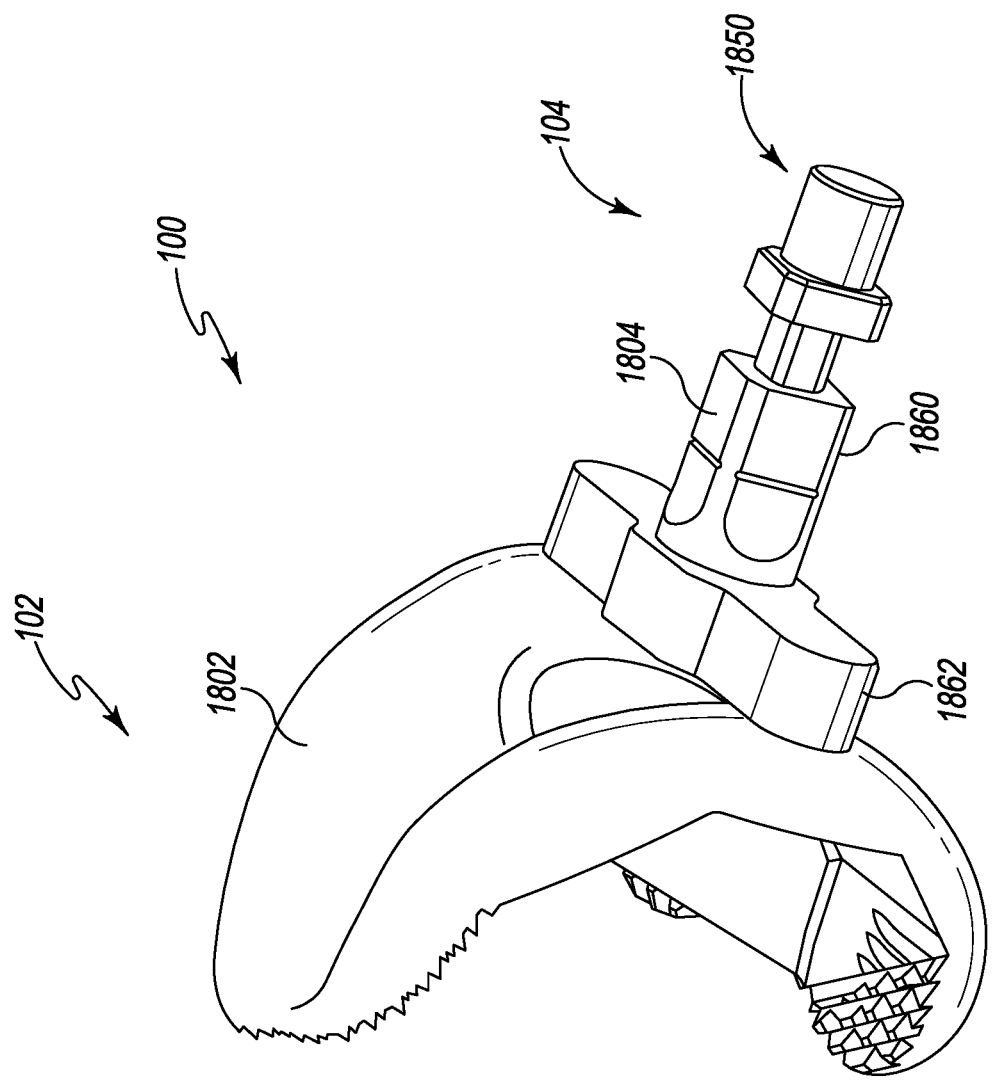
FIG. 20 is a perspective view of the femoral finishing rasp assembly of FIG. 19 having the impactor adaptor coupled to the femoral trial finishing rasp.
Figure 21:
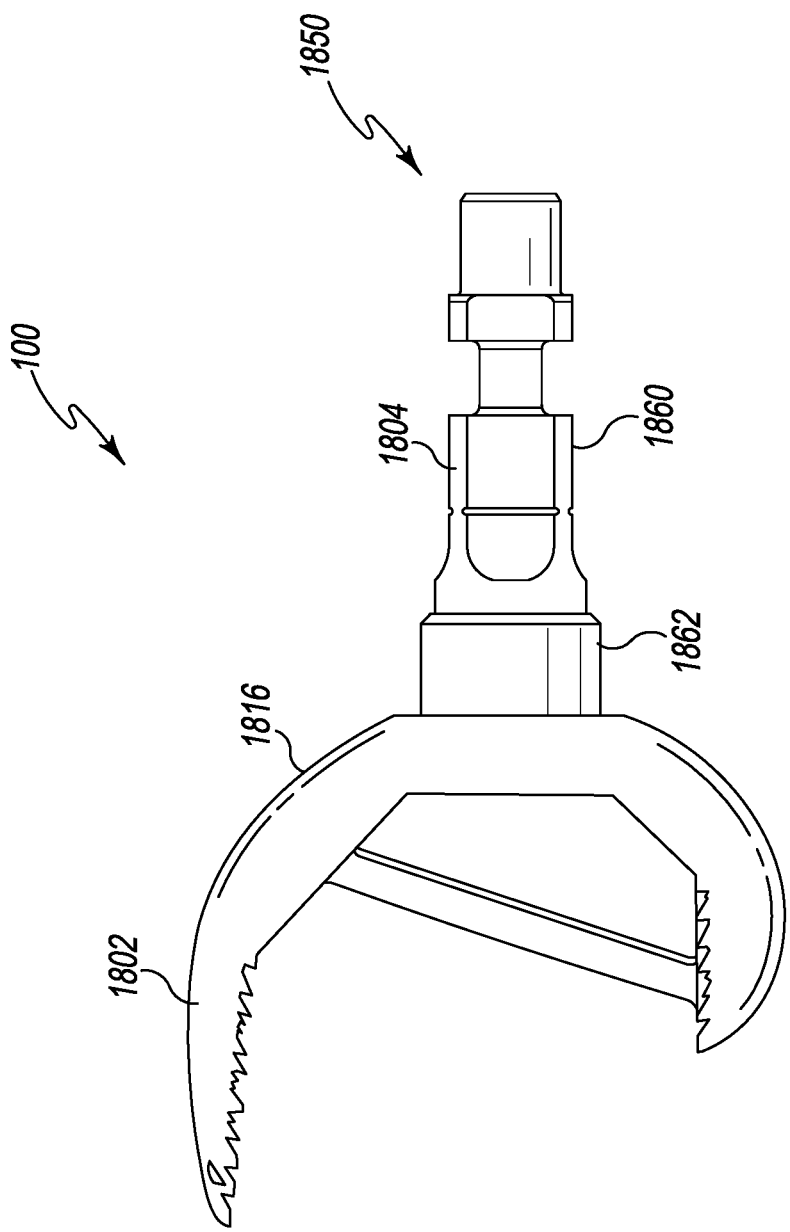
FIG. 21 is a side elevation view of the femoral finishing rasp assembly of FIG. 20.
Figure 22:
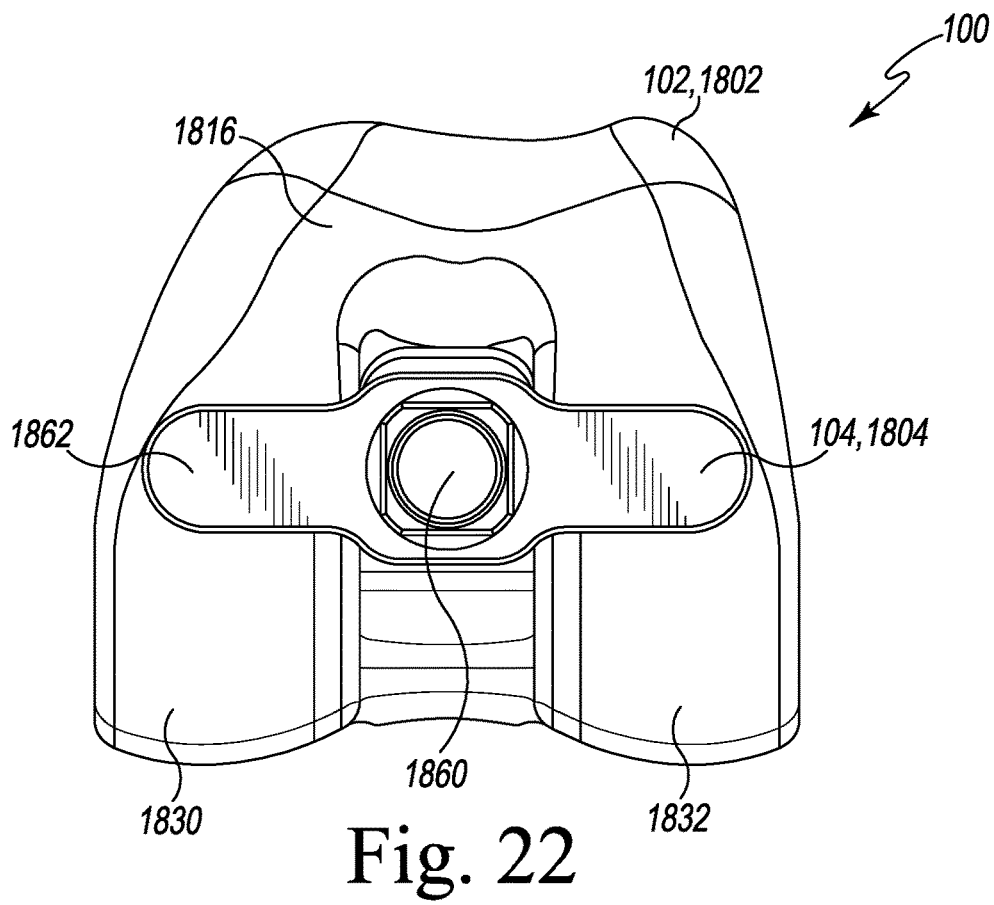
FIG. 22 is a distal, exterior elevation view of the femoral finishing rasp of FIG. 20.
Figure 23:
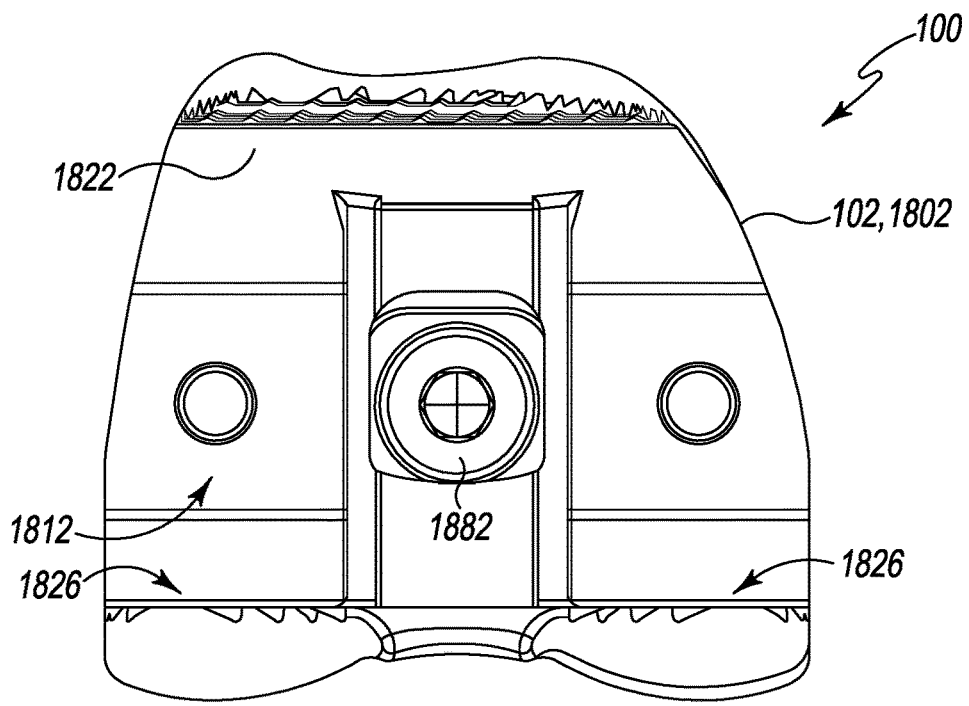
FIG. 23 is a proximal, interior elevation view of the femoral finishing rasp of FIG. 20.

The head 1862 also includes the connector 1892 defined on the proximal side 1872. As discussed above, the connector 1892 is configured (i.e., sized and shaped) to couple, or otherwise mate, with the connector 1890 of the femoral trial finishing rasp 1802 as shown in FIGS. 19 and 20. Illustratively, the connector 1892 is embodied as a pair of posts 1884 that extend away from the proximal side 1872 of the head 1862. The posts 1884 are positioned on the head 1862 such that each post 1884 is received in a corresponding one of the apertures 1836 defined in the medial and lateral femoral condyles 1830, 1832 of the femoral trial finishing rasp 1802 when the impactor adaptor 1804 is coupled to the femoral trial finishing rasp 1802. In the illustrative embodiment, each post 1884 includes a ball detent 1886, which is configured to secure the post 1884 within the respective aperture 1836 when the impactor adaptor 1804 is coupled to the femoral trial finishing rasp 1802. It should be appreciated, however, other mechanisms may be used to secure the impactor adaptor 1804 to the femoral trial finishing rasp 1802 in other embodiments.

Figure 24A:
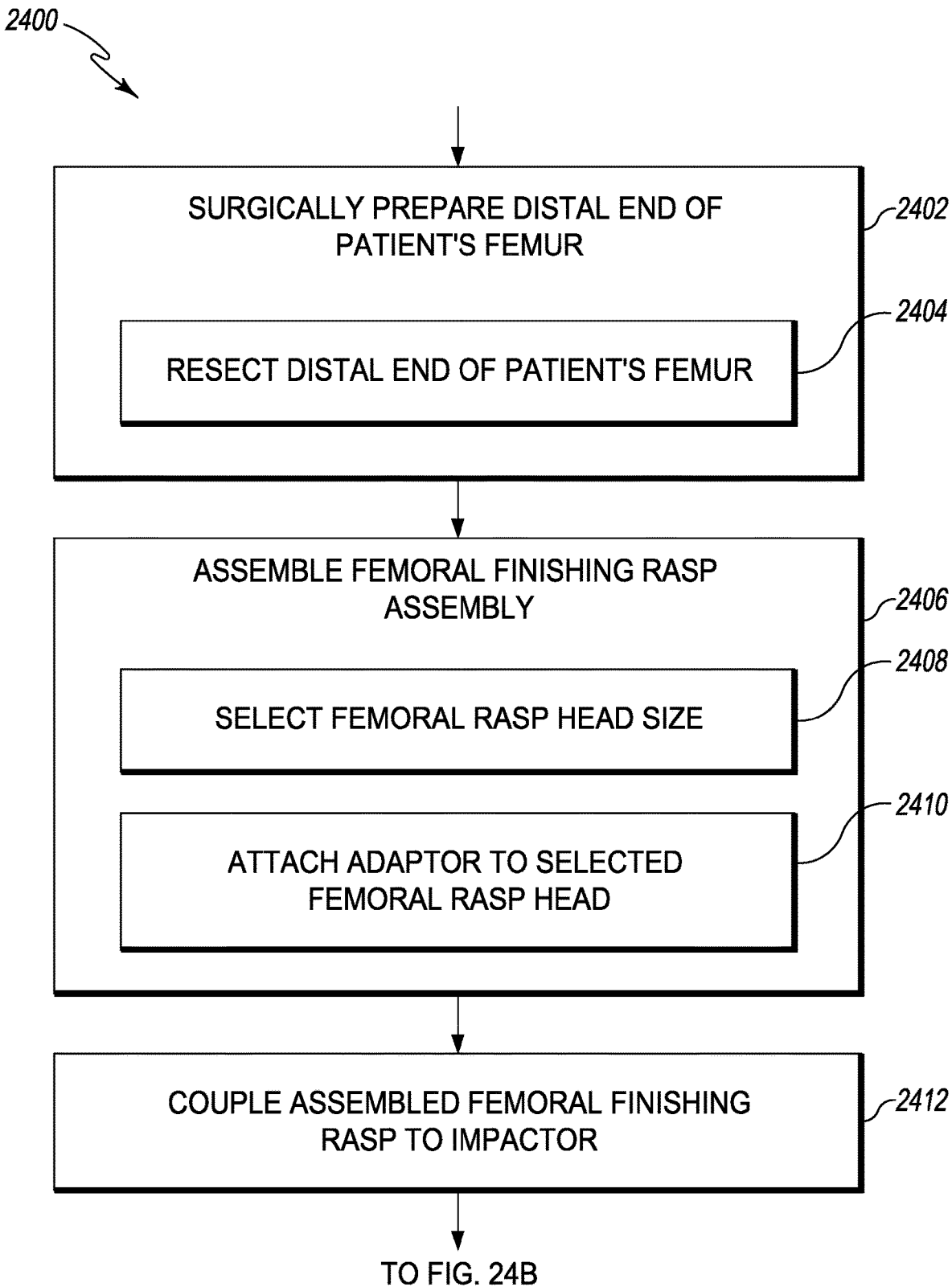
FIGS. 24A and 24B are a simplified flow diagram of an embodiment of a method for performing an orthopaedic surgical procedure on a patient's femur.
Figure 24B:
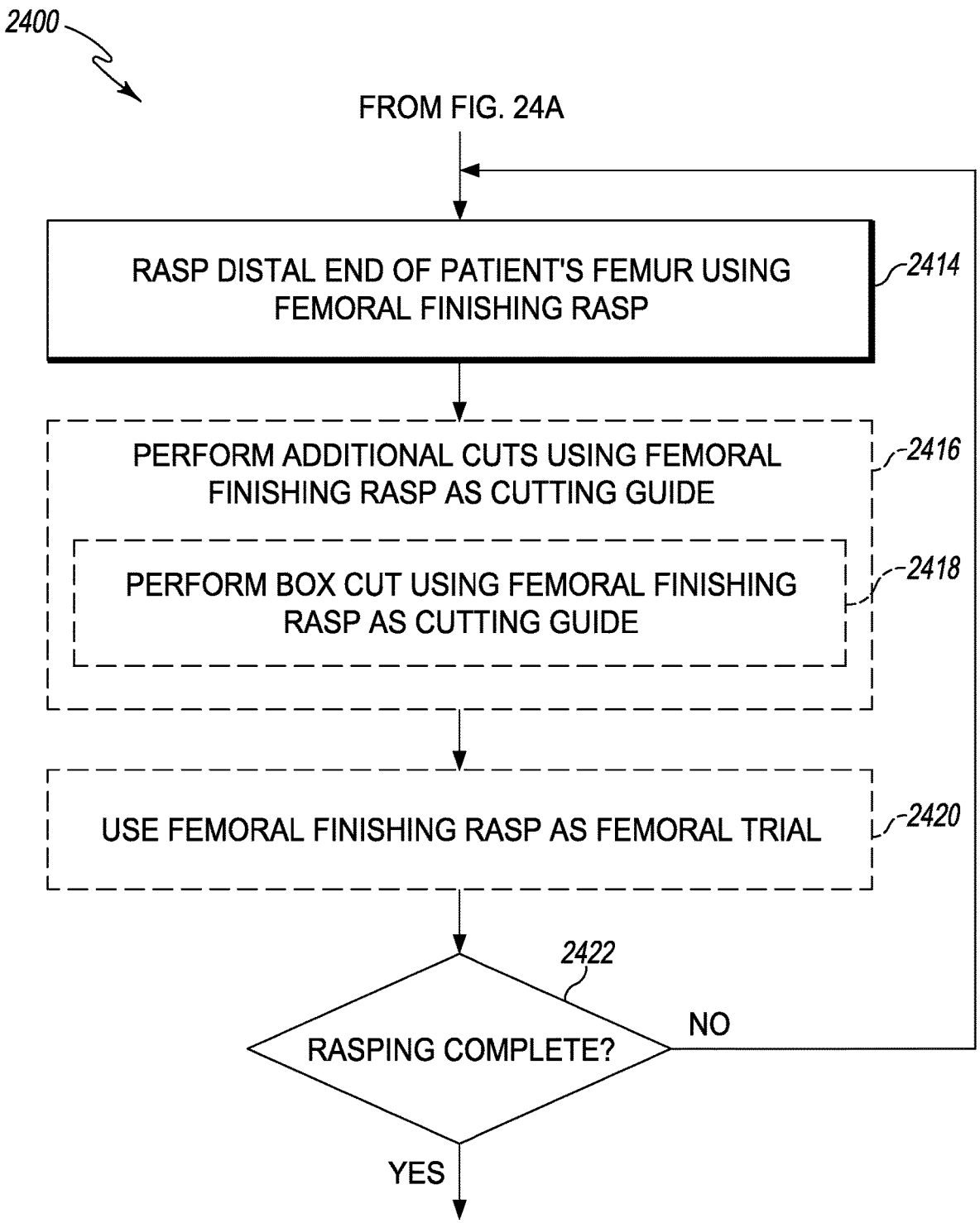

Referring now to FIGS. 24A and 24B, an orthopaedic surgeon may perform a method 2400 for performing an orthopaedic surgical procedure on a patient's femur using the femoral finishing rasp assembly 100 described above. The method 2400 begins with block 2402 in which the orthopaedic surgeon surgically prepares the patent's femur. For example, in block 2404 the orthopaedic surgeon may resect the patient's femur to prepare the femur for receiving an orthopaedic prosthesis. In doing so, the orthopaedic surgeon may perform a number of bone cuts on the distal end of the patient's femur including, for example, a distal cut, an anterior cut, a posterior cut, and chamfer cuts.

After the orthopaedic surgeon has surgically prepared the patient's femur in block 2402, the method 2400 advances to block 2406 in which the orthopedic surgeon assembles the femoral finishing rasp assembly 100. To do so, in block 2408, the orthopaedic surgeon may select a suitable femoral finishing rasp 102 from a collection of femoral finishing rasps 102. That is, the orthopaedic surgeon may select a femoral finishing rasp 102 that is appropriately sized for the patient's resected femur.

Subsequently, in block 2410, the orthopaedic surgeon attaches the impactor adaptor 104 to the selected femoral finishing rasp 102. To do so, in the embodiments illustrated in FIGS. 1-9, the orthopaedic surgeon may depress the handles 652 of the tabs 640, 642 of the connector 280 of the impactor adaptor 104 to cause the catches 656 to be retracted, insert the head of the 622 of the impactor adaptor 104 into the recess 198 of the connector 180, and release the handles 652 to allow the catches 656 to be biased outwardly into the apertures 186, 188 of the brackets 182, 184 of the connector 180 as indicated best in FIGS. 8 and 9. Alternatively, in the embodiments illustrated in FIGS. 13-17, the orthopaedic surgeon may insert the securing device 1300 through the passageway 1302 of the distal wall 124 of the body 110 of the femoral finishing rasp 102 and thread the securing device 1300 into the threaded aperture of the nub 1312 of the connector 180 of the impactor adaptor 104 as indicated in FIG. 13. Further, in the embodiments illustrated in FIGS. 18-23, the orthopaedic surgeon may first insert the securing device 1882 through the passageway 1878 of the head 1862 of the impactor adaptor 1804 and thread the securing device 1882 into the threaded aperture of the nub 1868 of the elongated shank 1860, while the nub 1868 is received in the receptacle 1880 of the head 1862 as best indicated in FIG. 18. Subsequently, the orthopaedic surgeon may couple the connector 1892 of the impactor adaptor 1804 to the connector 1890 of the femoral trial finishing rasp 1802 by inserting the posts 1884 of the head 1862 into the apertures 1836 defined in the defined in the medial and lateral femoral condyles 1830, 1832 of the femoral trial finishing rasp 1802 to thereby couple the impactor adaptor 1804 to the femoral trial finishing rasp 1802 as shown best in FIGS. 19 and 20.

In block 2412 of the method 2400, the orthopaedic surgeon couples the assembled femoral finishing rasp assembly 100 to an impactor. As discussed above, the impactor may be embodied as an automated impactor such as the automated impactor 1100 illustrated and described above in regard to FIG. 11 or embodied as a manual impactor such as the manual impactor 1200 illustrated and described above in regard to FIG. 12.

Referring now to bock 2414 of FIG. 24B, once the orthopaedic surgeon has assembled the femoral finishing rasp assembly 100 in block 2406 and coupled the assembled femoral finishing rasp assembly 100 to an impactor in block 2412, the orthopaedic surgeon may rasp the distal end of the patient's femur using the femoral finishing rasp assembly 100 and corresponding impactor. For example, in some embodiments, the orthopaedic surgeon may rasp the distal end of the patient's femur in a proximal-distal direction using the femoral finishing rasp assembly 100 and associated reciprocating impactor.

During or subsequent to the rasping procedure of block 2414, the orthopaedic surgeon may also perform additional cuts on the patient's femur using the femoral finishing rasp 102 as a cutting guide in block 2416, in some embodiments. For example, in embodiments including the femoral finishing rasp 102 of FIGS. 1-9, the orthopaedic surgeon may use the inner walls 166 of the distal wall 124 to as a box cutting guide to perform a box cut on the distal end of the patient's femur as shown in block 2418. Additionally, in embodiments in which the femoral finishing rasp assembly 100 include the femoral trial finishing rasp 1802 of FIGS. 18-23, the orthopaedic surgeon may use the articular side 1816 of the femoral trial finishing rasp 1802 as a femoral trial in block 2420. That is, the orthopaedic surgeon may utilize the medial and lateral femoral condyle surfaces 1830, 1832 as a femoral trial on the patient's natural or artificial tibia to monitor the developing mechanics of the patient's artificial knee joint.

Subsequently, in block 2422, the orthopaedic surgeon may assess whether additional rasping is complete or not. If not, the method 2400 loops back to 2414 in which the orthopaedic surgeon may continue rasping the distal end of the patient's femur using the femoral finishing rasp assembly 100. In doing so, in some embodiments, the orthopaedic surgeon may use different sized femoral finishing rasps 102 during each iteration, if needed. However, if the patient's femur is satisfactorily sized and shaped for the corresponding femoral prosthesis, the method 2400 is completed, and the orthopaedic surgeon may continue on with the orthopaedic surgical procedure.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the methods, apparatuses, and/or systems described herein. It will be noted that alternative embodiments of the methods, apparatuses, and systems of the present disclosure may not include all of the features described yet still benefit from at least some of the advantages of such features. Those of ordinary skill in the art may readily devise their own implementations of the methods, apparatuses, and systems that incorporate one or more of the features of the present invention and fall within the spirit and scope of the present disclosure as defined by the appended claims.

The invention claimed is:

1. A femoral finishing rasp assembly for use in an orthopaedic surgical procedure, the femoral finishing rasp assembly comprising:
   a femoral finishing rasp having a body that defines an interior cavity configured to receive a distal end of a patient's femur, wherein the body includes (i) an anterior wall having an interior surface facing the interior cavity and an exterior surface opposite the interior surface, wherein the interior surface of the anterior wall includes a first set of rasping teeth, (ii) a posterior wall opposite the anterior wall and having an interior surface facing the interior cavity and an exterior surface opposite the interior surface of the posterior wall, wherein the interior surface of the posterior wall includes a second set of rasping teeth, (iii) a distal wall having an anterior end connected to a distal end of the anterior wall and a posterior end connected to a distal end of the posterior wall, the distal wall including an interior surface facing the interior cavity and an exterior surface opposite the interior surface of the distal wall, and (iv) a connector attached to the exterior surface of the distal wall, wherein the distal wall includes a plurality of interior surfaces that cooperate to define an aperture extending through the distal wall and wherein the plurality of interior surfaces of the distal wall cooperate to define a femoral box cutting guide; and
   an impactor adaptor having a first end configured to be coupled to an orthopaedic impactor and a second end, opposite the first end, having a connector configured to selectively couple to the connector of the femoral finishing rasp.

2. The femoral finishing rasp assembly of claim 1, wherein the connector of the femoral finishing rasp includes a medial bracket extending distally from the exterior surface of the distal wall and a lateral bracket extending distally from the exterior surface of the distal wall, wherein the medial and lateral brackets are laterally spaced from each other and each medial and lateral bracket includes a corresponding aperture defined therethrough, wherein the aperture of the medial bracket and the aperture of the lateral bracket are coaxial with each other.

3. The femoral finishing rasp assembly of claim 2, wherein the aperture defined through the distal wall is located between the medial bracket and the lateral bracket.

4. The femoral finishing rasp assembly of claim 3, wherein the posterior wall includes an aperture defined therethrough and in fluid communication with the aperture of the distal wall, wherein the posterior wall comprises a medial posterior wall and a lateral posterior wall laterally spaced from the medial posterior wall by the aperture of the posterior wall.

5. The femoral finishing rasp assembly of claim 2, wherein the connector of the femoral finishing rasp further includes a plurality of sidewalls that cooperate with the medial bracket and the lateral bracket to define a recess configured to receive a head of the connector of the impactor adaptor.

6. A femoral finishing rasp assembly for use in an orthopaedic surgical procedure, the femoral finishing rasp assembly comprising:

a femoral finishing rasp having a body that defines an interior cavity configured to receive a distal end of a patient's femur, wherein the body includes (i) an anterior wall having an interior surface facing the interior cavity and an exterior surface opposite the interior surface, wherein the interior surface of the anterior wall includes a first set of rasping teeth, (ii) a posterior wall opposite the anterior wall and having an interior surface facing the interior cavity and an exterior surface opposite the interior surface of the posterior wall, wherein the interior surface of the posterior wall includes a second set of rasping teeth, (iii) a distal wall having an anterior end connected to a distal end of the anterior wall and a posterior end connected to a distal end of the posterior wall, the distal wall including an interior surface facing the interior cavity and an exterior surface opposite the interior surface of the distal wall, and (iv) a connector attached to the exterior surface of the distal wall; and an impactor adaptor having a first end configured to be coupled to an orthopaedic impactor and a second end, opposite the first end, having a connector configured to selectively couple to the connector of the femoral finishing rasp, wherein the connector of the femoral finishing rasp includes a medial bracket extending distally from the exterior surface of the distal wall and a lateral bracket extending distally from the exterior surface of the distal wall, wherein the medial and lateral brackets are laterally spaced from each other and each medial and lateral bracket includes a corresponding aperture defined therethrough, wherein the aperture of the medial bracket and the aperture of the lateral bracket are coaxial with each other, and wherein the connector of the impactor adaptor includes a first and second tab, wherein each of the first and second tabs includes a catch, and wherein, when the connector of the impactor adaptor is coupled to the connector of the femoral finishing rasp, the catch of the first tab is received in the aperture of the medial bracket of the connector of the femoral finishing rasp and the catch of the second tab is received in the aperture of the lateral bracket of the connector of the femoral finishing rasp.

7. The femoral finishing rasp assembly of claim 6, wherein the first tab and the second tab are biased outwardly away each other and each of the first tab and the second tab is movable in an inwardly direction to cause movement of the associated catch from the aperture of the corresponding medial and lateral bracket to decouple the connector of the impactor adaptor from the connector of the femoral finishing rasp.

8. The femoral finishing rasp assembly of claim 7, wherein the connector of the impactor adaptor includes a pair of tracks and each of the first tab and the second tab is positioned in a corresponding track of the pair of tracks, and wherein each of the first tab and the second tab is movable in the corresponding track to couple or decouple the connector of the impactor adaptor and the connector of the femoral finishing rasp.

9. The femoral finishing rasp assembly of claim 6, wherein the aperture defined through the distal wall is located between the medial bracket and the lateral bracket, and wherein the posterior wall includes an aperture defined therethrough and in fluid communication with the aperture of the distal wall, wherein the posterior wall comprises a medial posterior wall and a lateral posterior wall laterally spaced from the medial posterior wall by the aperture of the posterior wall.

10. A femoral finishing rasp assembly for use in an orthopaedic surgical procedure, the femoral finishing rasp assembly comprising:

a femoral finishing rasp having a body that defines an interior cavity configured to receive a distal end of a patient's femur, wherein the body includes (i) an anterior wall having an interior surface facing the interior cavity and an exterior surface opposite the interior surface, wherein the interior surface of the anterior wall includes a first set of rasping teeth, (ii) a posterior wall opposite the anterior wall and having an interior surface facing the interior cavity and an exterior surface opposite the interior surface of the posterior wall, wherein the interior surface of the posterior wall includes a second set of rasping teeth, (iii) a distal wall having an anterior end connected to a distal end of the anterior wall and a posterior end connected to a distal end of the posterior wall, the distal wall including an interior surface facing the interior cavity and an exterior surface opposite the interior surface of the distal wall, and (iv) a connector attached to the exterior surface of the distal wall;

an impactor adaptor having a first end configured to be coupled to an orthopaedic impactor and a second end, opposite the first end, having a connector configured to selectively couple to the connector of the femoral finishing rasp; and a securing device, wherein the distal wall of the femoral finishing rasp includes a passageway defined therethrough and the second end of the impactor adaptor includes an aperture defined therein, and wherein the securing device is configured to be received through the passageway of the distal wall and into the aperture of the second end of the impactor adaptor to secure the femoral finishing rasp to the impactor adaptor.

11. A femoral finishing rasp assembly for use in an orthopaedic surgical procedure, the femoral finishing rasp assembly comprising:

a femoral finishing rasp having a body that includes an articular side and a rasping side opposite the articular side, wherein the articular side comprises a femoral trial surface that includes a medial femoral condyle surface having a curved contour and a lateral femoral condyle surface having a curved contour and spaced apart from the medial femoral condyle, and wherein the rasping side comprises a plurality of surfaces including an anterior rasping surface including a first set of rasping teeth, a medial posterior rasping surface including a second set of rasping teeth, and a lateral posterior rasping surface including a third set of rasping teeth; and an impactor adaptor having a first end configured to be coupled to an orthopaedic impactor and a second end, opposite the first end, having a connector configured to selectively couple to the articular side of the femoral finishing rasp.

12. The femoral finishing rasp assembly of claim 11, wherein the impactor adaptor comprises a shank and a head separate from the shank, wherein the shank includes the first end configured to be coupled to the orthopaedic impactor and the head includes the second end having the connector configured to selectively couple to the articular side of the femoral finishing rasp.

13. The femoral finishing rasp assembly of claim 12, wherein the impactor adaptor further comprises a securing device, the head includes a passageway defined therethrough, and the shank includes a mounting end, opposite the first end, having an aperture defined therein, and wherein the securing device is configured to be received through the passageway of the head and into the aperture of the mounting end of the shank to secure the head to the shank.

14. The femoral finishing rasp assembly of claim 12, wherein the articular side of the body of the femoral finishing rasp includes a pair of apertures defined therein, and wherein the connector of the impactor adaptor includes a pair of posts extending outwardly from the head, wherein each post is configured to be received in a corresponding aperture of the pair of apertures of the articular side of the femoral finishing rasp when the impactor adaptor is coupled to the femoral finishing rasp.

15. The femoral finishing rasp assembly of claim 14, wherein each post of the pair of posts includes a ball detent configured to secure the impactor adaptor to the femoral finishing rasp when the posts are received in the apertures of the articular side of the femoral finishing rasp.

16. A femoral finishing rasp assembly for use in an orthopaedic surgical procedure, the femoral finishing rasp assembly comprising:

a femoral finishing rasp having a body that includes an articular side and a rasping side opposite the articular side, wherein the articular side of comprises (i) a medial femoral condyle surface having a curved contour, (ii) a lateral femoral condyle surface having a curved contour and spaced apart from the medial femoral condyle, and (iii) a pair of apertures defined therein and wherein the rasping side comprises a plurality of surfaces including an anterior rasping surface including a first set of rasping teeth, a medial posterior rasping surface including a second set of rasping teeth, and a lateral posterior rasping surface including a third set of rasping teeth; and an impactor adaptor comprising (i) a shank having a first end configured to be coupled to an orthopaedic impactor, (ii) a head separate from the shank and including a second end having a connector configured to selectively couple to the articular side of the femoral finishing rasp, and a pair of posts extending outwardly from the head, wherein each post is configured to be received in a corresponding aperture of the pair of apertures of the articular side of the femoral finishing rasp when the impactor adaptor is coupled to the femoral finishing rasp.

17. The femoral finishing rasp assembly of claim 16, wherein each post of the pair of posts includes a ball detent configured to secure the impactor adaptor to the femoral finishing rasp when the posts are received in the apertures of the articular side of the femoral finishing rasp.

18. The femoral finishing rasp assembly of claim 16, wherein the articular side of the femoral finishing rasp comprises a femoral trial surface.

19. The femoral finishing rasp assembly of claim 16, wherein the impactor adaptor further comprises a securing device, the head includes a passageway defined therethrough, and the shank includes a mounting end, opposite the first end, having an aperture defined therein, and wherein the securing device is configured to be received through the passageway of the head and into the aperture of the mounting end of the shank to secure the head to the shank.

* * * * *